(12) United States Patent
Haupfear et al.

(10) Patent No.: US 7,179,936 B2
(45) Date of Patent: Feb. 20, 2007

(54) PROCESS FOR RECOVERING A CRYSTALLINE PRODUCT FROM SOLUTION

(75) Inventors: Eric A. Haupfear, St. Charles, MO (US); Eduardo A. Casanova, Chesterfield, MO (US); Kenneth S. Meyer, Muscatine, IA (US); Henry H. Chien, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 238 days.

(21) Appl. No.: 10/943,783

(22) Filed: Sep. 17, 2004

(65) Prior Publication Data

US 2005/0059840 A1    Mar. 17, 2005

Related U.S. Application Data

(60) Provisional application No. 60/558,518, filed on Mar. 31, 2004, provisional application No. 60/504,466, filed on Sep. 17, 2003.

(51) Int. Cl.
*C07F 9/22* (2006.01)
*C07F 9/28* (2006.01)

(52) U.S. Cl. ........................... 562/17
(58) Field of Classification Search ............ 562/17
See application file for complete search history.

(56) References Cited

U.S. PATENT DOCUMENTS

| | | | |
|---|---|---|---|
| 3,799,758 A | 3/1974 | Franz | |
| 3,950,402 A | 4/1976 | Franz | |
| 3,969,398 A | 7/1976 | Hershman | |
| 4,582,650 A | 4/1986 | Felthouse | |
| 4,624,937 A | 11/1986 | Chou | |
| 4,696,772 A | 9/1987 | Chou | |
| 4,983,764 A * | 1/1991 | Pelyva et al. | 562/17 |
| 5,041,628 A * | 8/1991 | Donadello | 562/17 |
| 5,087,740 A | 2/1992 | Smith | |
| 5,179,228 A | 1/1993 | Ramon et al. | |
| 6,417,133 B1 | 7/2002 | Ebner et al. | |
| 6,586,621 B2 | 7/2003 | Leiber et al. | |
| 6,730,813 B2 * | 5/2004 | Hitzler et al. | 568/17 |
| 6,927,304 B2 * | 8/2005 | Leiber | 562/17 |
| 2002/0068836 A1 | 6/2002 | Haupfear et al. | |

FOREIGN PATENT DOCUMENTS

| | | |
|---|---|---|
| WO | WO 00/01707 A1 | 1/2000 |
| WO | WO 01/92272 A2 | 12/2001 |

OTHER PUBLICATIONS

Franz, et al., Glyphosate: A Unique Global Herbicide, ACS Monograph 189, 1997, pp. 233-262.

* cited by examiner

*Primary Examiner*—Thurman K. Page
*Assistant Examiner*—Chukwuma Nwaonicha
(74) *Attorney, Agent, or Firm*—Senniger Powers; Joseph A. Schaper

(57) ABSTRACT

An improved process for recovering a crystalline product (particularly an N-(phosphonomethyl)glycine product) from a solution comprising both a product subject to crystallization and undesired impurities is provided.

40 Claims, 6 Drawing Sheets

US 7,179,936 B2

PROCESS FOR RECOVERING A CRYSTALLINE PRODUCT FROM SOLUTION

REFERENCE TO RELATED APPLICATIONS

This application claims the benefit of U.S. Provisional Application Ser. No. 60/504,466, filed Sep. 17, 2003, and U.S. Provisional Application Ser. No. 60/558,518, filed Mar. 31, 2004, the entire contents of which are incorporated herein by reference.

FIELD OF THE INVENTION

The present invention relates generally to processes for producing and recovering a crystalline product from a solution comprising a product subject to crystallization and undesired impurities. More particularly, the invention relates to processes for producing and recovering N-(phosphonomethyl)glycine products from aqueous reaction solutions prepared by the liquid phase oxidation of N-(phosphonomethyl)iminodiacetic acid substrates.

BACKGROUND OF THE INVENTION

N-(phosphonomethyl)glycine is described by Franz in U.S. Pat. No. 3,799,758. N-(phosphonomethyl)glycine and its salts are conveniently applied as a component of aqueous, post-emergent herbicide formulations. As such, they are particularly useful as a highly effective and commercially important broad-spectrum herbicide for killing or controlling the growth of a wide variety of plants, including germinating seeds, emerging seedlings, maturing and established woody and herbaceous vegetation and aquatic plants.

One of the more widely accepted methods of making N-(phosphonomethyl)glycine products includes the liquid phase oxidative cleavage of a carboxymethyl substituent from an N-(phosphonomethyl)iminodiacetic acid substrate. As used herein, "N-(phosphonomethyl)iminodiacetic acid substrates" include N-(phosphonomethyl)iminodiacetic acid and salts thereof, wherein the salt-forming cation is, for example, ammonium, alkylammonium, an alkali metal or an alkaline earth metal. Over the years, a wide variety of methods and reactor systems have been disclosed for conducting this oxidation reaction. See generally, Franz, et al., *Glyphosate: A Unique Global Herbicide* (ACS Monograph 189, 1997) at pp. 233–62 (and references cited therein); Franz, U.S. Pat. No. 3,950,402; Hershman, U.S. Pat. No. 3,969,398; Felthouse, U.S. Pat. No. 4,582,650; Chou, U.S. Pat. No. 4,624,937; Chou, U.S. Pat. No. 4,696,772; Ramon et al., U.S. Pat. No. 5,179,228; Siebenhaar et al., International Publication No. WO 00/01707; Ebner et al., U.S. Pat. No. 6,417,133; Leiber et al., U.S. Pat. No. 6,586,621; and Haupfear et al., International Publication No. WO 01/92272.

The liquid phase oxidation of an N-(phosphonomethyl)iminodiacetic acid substrate typically produces a reaction mixture containing water and various impurities besides the desired N-(phosphonomethyl)glycine product. These impurities may include, for example, various by-products, unreacted starting materials, as well as impurities present in the starting materials. Representative examples of impurities present in N-(phosphonomethyl)glycine product reaction mixtures include unreacted N-(phosphonomethyl)iminodiacetic acid substrate, N-formyl-N-(phosphonomethyl)glycine, phosphoric acid, phosphorous acid, hexamethylenetetraamine, aminomethylphosphonic acid (AMPA), methyl aminomethylphosphonic acid (MAMPA), iminodiacetic acid (IDA), formaldehyde, formic acid, chlorides and the like. The value of the N-(phosphonomethyl)glycine product normally dictates maximal recovery of the product from the reaction mixture and also often provides incentive for recycling at least a portion of the depleted reaction mixture (e.g., to the oxidation reactor system) for further conversion of unreacted substrate and recovery of product.

Commercial considerations also sometimes dictate that the concentration of the N-(phosphonomethyl)glycine product in the commercially sold mixtures be significantly greater than the concentrations in the reaction mixtures that are typically formed in the oxidation reactor system, particularly where the N-(phosphonomethyl)glycine product is being stored or shipped for agricultural applications. For example, when a heterogeneous catalyst is used for the liquid phase oxidation of N-(phosphonomethyl)iminodiacetic acid to make the N-(phosphonomethyl)glycine as described by Haupfear et al. in International Publication No. WO 01/92272, it is typically preferred to maintain a maximum concentration of the N-(phosphonomethyl)glycine product in the reaction mixture of no greater than about 9% by weight in order to keep the product solubilized, although higher concentrations in excess of 9% and even up to about 12% by weight may be suitably utilized at higher reaction mixture temperatures. Sometimes, however, it is desirable for the commercially sold mixtures to have an N-(phosphonomethyl)glycine concentration that is significantly greater. Thus, after the N-(phosphonomethyl)glycine product has been formed and, if necessary, separated from the catalyst, it is typically preferable to concentrate the product and separate the product from the various impurities in the oxidation reaction mixture.

Smith, in U.S. Pat. No. 5,087,740, describes one process for purifying and concentrating an N-(phosphonomethyl)glycine product. Smith discloses passing a reaction mixture containing N-(phosphonomethyl)glycine through a first ion exchange resin column to remove impurities that are more acidic than the N-(phosphonomethyl)glycine, passing the effluent from the first ion exchange resin column through a second ion exchange resin column which adsorbs the N-(phosphonomethyl)glycine, and recovering the N-(phosphonomethyl)glycine by passing a base or strong mineral acid through the second ion exchange resin column.

Haupfear et al., in International Publication No. WO01/92272, describe processes for purifying and concentrating an N-(phosphonomethyl)glycine product prepared by the oxidation of N-(phosphonomethyl)iminodiacetic acid substrates. Haupfear et al. describe generating two crystalline N-(phosphonomethyl)glycine products in two separate crystallizers wherein the crystals have two distinct purities. The lower purity material may then be blended with the higher purity material to produce a single product of acceptable purity.

There remains a need for processes for producing and recovering a crystalline product from a solution comprising a product subject to crystallization and undesired impurities that is capable of producing multiple product mixtures containing the crystalline product, each exhibiting a suitable impurity profile for the intended use. Particularly a need exists for processes for producing and recovering a crystalline N-(phosphonomethyl)glycine product from a reaction solution prepared by the oxidation of an N-(phosphonomethyl)iminodiacetic acid substrate capable of producing both a saleable N-(phosphonomethyl)glycine wet-cake product as well as concentrated liquid or solid salts of N-(phosphonomethyl)glycine of acceptable purity for use in formulation of herbicidal compositions. Such a process would improve overall flexibility to adequately support market demand for various N-(phosphonomethyl)glycine products

SUMMARY OF THE INVENTION

Among certain objects of the present invention, therefore, are the provision of an improved process for the recovery of one or more crystalline products from a solution comprising both a product subject to crystallization from the solution and undesired impurities; the provision of such a process wherein one or more crystalline products of acceptable purity may be produced without washing the crystalline product; the provision of such a process which is capable of recovering one or more crystalline products of acceptable purity when cake washing is insufficient to remove occluded impurities from the crystalline product; the provision of a process for recovering one or more N-(phosphonomethyl) glycine products from a slurry comprising precipitated N-(phosphonomethyl)glycine product crystals and a mother liquor; the provision of such a process capable of producing a plurality of suitable crystalline products, for example, multiple wet-cake products, thereby providing for greater process flexibility; and the provision of such a process that can recover crystalline products of acceptable purity having better handling and packaging characteristics.

Briefly, therefore, one aspect of the present invention is directed to processes for preparing a plurality of crystalline products, for example, multiple wet-cake products, from a solution comprising both a product subject to crystallization from the solution and undesired impurities. In one embodiment, the process comprises dividing the solution into plural fractions comprising a primary fraction and a secondary fraction and precipitating product crystals from the primary fraction in a first crystallization operation to produce a primary product slurry comprising precipitated product crystals and a primary mother liquor. Product crystals are also precipitated from the secondary fraction in a second crystallization operation to produce a secondary product slurry comprising precipitated product crystals and a secondary mother liquor. Precipitated product crystals are separated from the primary product slurry in a first liquid/solids separation step to produce a first wet-cake product and a primary mother liquor fraction. Precipitated product crystals are also separated from the secondary product slurry in a second liquid/solids separation step to produce a second wet-cake product and a secondary mother liquor fraction. At least a part of each of the mother liquor fractions is recycled so that unrecovered product and impurities contained therein are reintroduced into one or both of the crystallization operations. Furthermore, the impurity content of each of the wet-cake products is managed or maintained below a defined value by (i) net transfer of impurities contained in one of the first and second mother liquor fractions to the other of the first and second crystallization operations; (ii) net transfer of impurities contained in one of the first and second mother liquor fractions to the other of the first and second liquid/solids separation steps; (iii) net transfer of wet-cake product of relatively low impurities content, as obtained from one of the first and second liquid/solids separation steps, to the other of the first and second crystallization operations; (iv) net transfer of wet-cake product of relatively low impurities content, as obtained from one of the first and second liquid/solids separation steps, to the other of the first and second liquid/solids separation steps; (v) net transfer of slurry of relatively low impurities content, as obtained in one of the first and second crystallization operations, to the other of the first and second crystallization operations; (vi) net transfer of slurry of relatively low impurities content, as obtained in one of the first and second crystallization operations, to the other of the first and second liquid/solids separation steps; or a combination of (i), (ii), (iii), (iv), (v) and/or (vi).

The present invention is particularly directed to processes for recovering one or more crystalline N-(phosphonomethyl)glycine products, for example, multiple wet-cake products, from an aqueous oxidation reaction solution comprising an N-(phosphonomethyl)glycine product in which impurity distribution among crystalline N-(phosphonomethyl)glycine wet-cake products is managed.

In one such embodiment, the aqueous reaction solution comprising N-(phosphonomethyl)glycine product is first divided into plural fractions comprising a primary fraction and a secondary fraction. N-(phosphonomethyl)glycine product crystals are precipitated from the primary fraction to produce a primary product slurry comprising precipitated N-(phosphonomethyl)glycine product crystals and a primary mother liquor. The primary product slurry is divided into a first portion and a second portion and precipitated N-(phosphonomethyl)glycine product crystals are separated from the first portion of the primary product slurry, thereby producing a first N-(phosphonomethyl)glycine wet-cake product. The second portion of the primary product slurry is combined with N-(phosphonomethyl)glycine product contained in or obtained from the secondary fraction of the aqueous reaction solution. The secondary fraction of the aqueous reaction solution is subjected to an evaporative crystallization operation to precipitate N-(phosphonomethyl)glycine product crystals from the secondary fraction, thereby producing a secondary evaporative product slurry comprising precipitated N-(phosphonomethyl)glycine product crystals and a secondary mother liquor. Separation of precipitated N-(phosphonomethyl)glycine product crystals from the secondary evaporative product slurry produces a second N-(phosphonomethyl)glycine wet-cake product.

In another embodiment of the invention, the process for recovering an N-(phosphonomethyl)glycine product from an aqueous oxidation reaction solution comprising an N-(phosphonomethyl)glycine product comprises dividing the aqueous reaction solution into plural fractions comprising a primary fraction and a secondary fraction. N-(phosphonomethyl)glycine product crystals are precipitated from the primary fraction to produce a primary product slurry comprising precipitated N-(phosphonomethyl)glycine product crystals and a primary mother liquor. Precipitated N-(phosphonomethyl)glycine product crystals are separated from the primary product slurry to produce a first N-(phosphonomethyl)glycine wet-cake product. At least a portion of the first N-(phosphonomethyl)glycine wet-cake product is combined with N-(phosphonomethyl)glycine product contained in or obtained from the secondary fraction of the aqueous reaction solution. N-(phosphonomethyl)glycine product crystals are precipitated from the secondary fraction of the aqueous reaction solution in an evaporative crystallization operation to produce a secondary evaporative product slurry comprising precipitated N-(phosphonomethyl)glycine product crystals and a secondary mother liquor. Precipitated N-(phosphonomethyl)glycine product crystals are separated from the secondary evaporative product slurry to obtain a second N-(phosphonomethyl)glycine wet-cake product.

In a further embodiment of the invention, the process for recovering an N-(phosphonomethyl)glycine product from an aqueous oxidation reaction solution comprising an N-(phosphonomethyl)glycine product comprises dividing the aqueous reaction solution into plural fractions comprising a primary fraction and a secondary fraction. N-(phosphonomethyl)glycine product crystals are precipitated from the primary fraction to produce a primary product slurry comprising precipitated N-(phosphonomethyl)glycine product crystals and a primary mother liquor. N-(phosphonomethyl) glycine product crystals are also separated from a secondary crystallization feed mixture comprising the secondary fraction of the aqueous reaction solution and at least a portion of the primary product slurry to produce a secondary product slurry comprising precipitated N-(phosphonomethyl)glycine product crystals and a secondary mother liquor. Precipitated N-(phosphonomethyl)glycine product crystals are separated from the secondary product slurry to produce an N-(phosphonomethyl)glycine wet-cake product.

In a further embodiment, the process for recovering an N-(phosphonomethyl)glycine product from an aqueous oxidation reaction solution comprising an N-(phosphonomethyl)glycine product includes dividing the aqueous reaction solution into plural fractions comprising a primary fraction and a secondary fraction and precipitating N-(phosphonomethyl)glycine product crystals from the primary fraction to produce a primary product slurry comprising precipitated N-(phosphonomethyl)glycine product crystals and a primary mother liquor. N-(phosphonomethyl)glycine product crystals are also precipitated from an aqueous secondary crystallization feed mixture comprising the secondary fraction of the aqueous reaction solution to produce a secondary product slurry comprising precipitated N-(phosphonomethyl) glycine product crystals and a secondary mother liquor. At least a portion of the primary product slurry is combined with at least a portion of the secondary product slurry to produce a secondary fraction product mixture from which precipitated N-(phosphonomethyl)glycine product crystals are separated to produce an N-(phosphonomethyl)glycine wet-cake product.

In a still further embodiment of the present invention, the process for recovering an N-(phosphonomethyl)glycine product from an aqueous oxidation reaction solution comprising an N-(phosphonomethyl)glycine product comprises dividing the aqueous reaction solution into plural fractions comprising a primary fraction and a secondary fraction and precipitating N-(phosphonomethyl)glycine product crystals from the primary fraction in a first crystallization operation to produce a primary product slurry comprising precipitated N-(phosphonomethyl)glycine product crystals and a primary mother liquor. N-(phosphonomethyl)glycine product crystals are also precipitated from the secondary fraction of the aqueous reaction solution in a second crystallization operation to produce a secondary product slurry comprising precipitated N-(phosphonomethyl)glycine product crystals and a secondary mother liquor. Precipitated N-(phosphonomethyl)glycine product crystals are separated from the primary product slurry in a first liquid/solids separation step to produce a first wet-cake product and a primary mother liquor fraction and precipitated N-(phosphonomethyl)glycine product crystals are separated from the secondary product slurry in a second liquid/solids separation step to produce a second wet-cake product and a secondary mother liquor fraction. At least a part of each of the mother liquor fractions is recycled so that unrecovered N-(phosphonomethyl)glycine product and impurities contained therein are reintroduced into one or both of the crystallization operations. Furthermore, the impurity content of each of the wet-cake products is maintained below a defined value by net transfer of impurities contained in one of the first and second mother liquor fractions to: (i) the other of the first and second crystallization operations; (ii) the other of the first and second liquid/solids separation steps; (iii) the other of the first and second wet-cake products; or any combination of (i), (ii) and/or (iii).

The present invention is also directed to processes for recovering an N-(phosphonomethyl)glycine product from a slurry comprising precipitated N-(phosphonomethyl)glycine product crystals and a mother liquor. In a first embodiment, the process comprises dividing the slurry into plural fractions comprising a first slurry fraction and a second slurry fraction. Precipitated N-(phosphonomethyl)glycine product crystals are separated from the first and second slurry fractions to produce a first wet-cake product and a second wet-cake product, respectively. The ratio of solids content of the second wet-cake product to the solids content of the first wet-cake product, as measured by weight percent of solids in the first and second wet-cake products, is at least about 1.1.

In another embodiment, the process for recovering an N-(phosphonomethyl)glycine product from a slurry comprising precipitated N-(phosphonomethyl)glycine product crystals and a mother liquor comprises dividing the slurry into plural fractions comprising first and second slurry fractions. The first slurry fraction is introduced into a first liquid/solids separation device in which precipitated N-(phosphonomethyl)glycine product crystals are separated from the first slurry fraction to produce a first wet-cake product. The second slurry fraction is introduced into a second liquid/solids separation device in parallel with the first liquid/solids separation device and in which precipitated N-(phosphonomethyl)glycine product crystals are separated from the second slurry fraction to produce a second wet-cake product. The second wet-cake product has a greater solids content than the first wet-cake product as measured by weight percent of solids in the wet-cake products.

Other objects and features of this invention will be in part apparent and in part pointed out hereinafter.

DETAILED DESCRIPTION OF THE PREFERRED EMBODIMENTS

Figure 1:
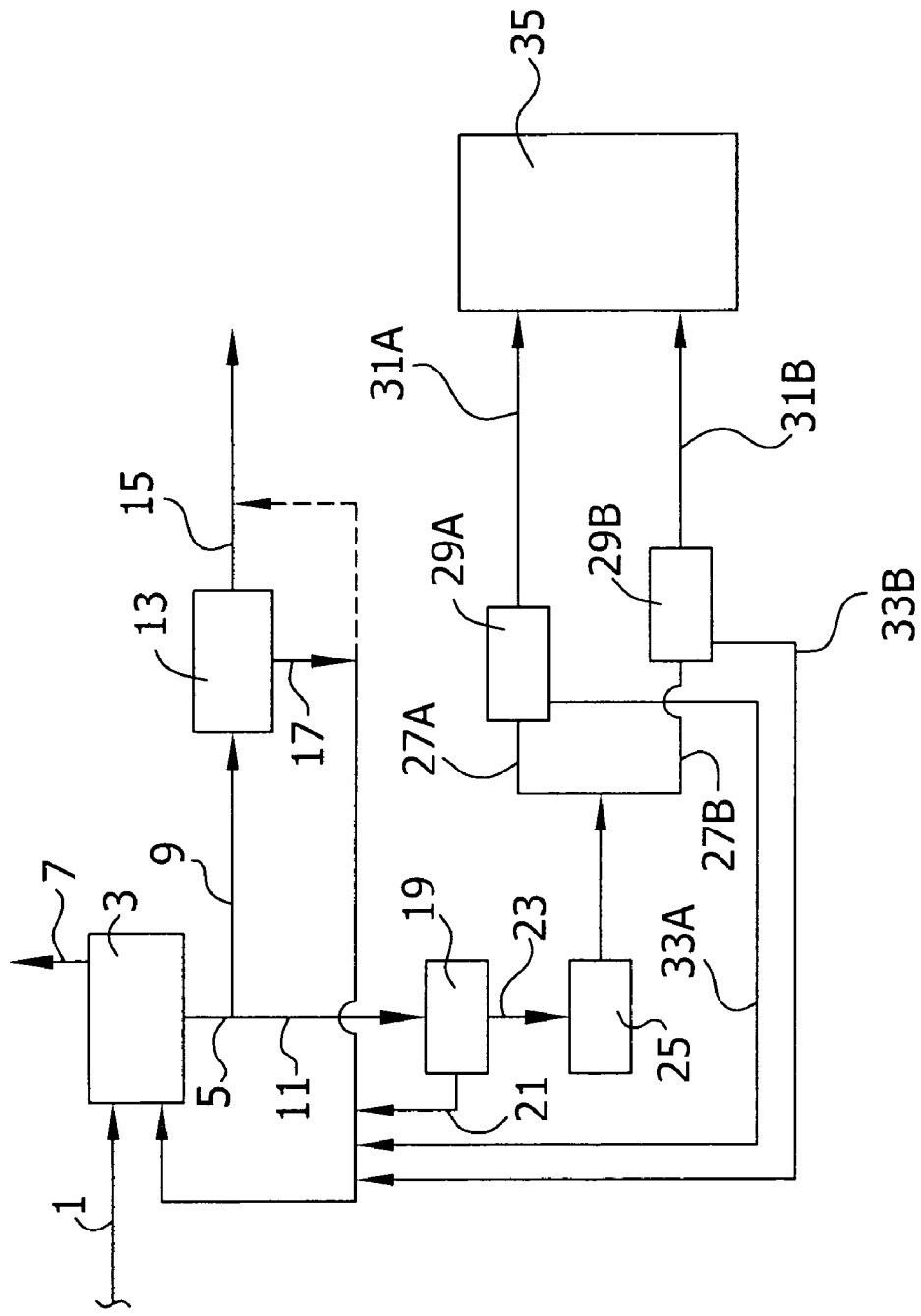
FIG. 1 is a schematic flow sheet of one embodiment of the present invention employing two separate liquid/solids separation systems or devices in parallel for the recovery of wet-cake products having different solids contents from a product slurry produced by concentrating a solution containing a product subject to crystallization therefrom in a crystallization stage.

In accordance with the present invention, improvements in processes for producing and recovering multiple crystalline wet-cake products (particularly N-(phosphonomethyl)glycine wet-cake products) from one or more solutions comprising both a product subject to crystallization and undesired impurities have been discovered. Typically, at least one of the crystalline products recovered is of acceptable purity, and any other crystalline products recovered are of acceptable purity, can be blended with one or more other crystalline products to form a product of acceptable purity, and/or can be further processed or blended to form a wet-cake or concentrated liquid or solid salts of N-(phosphonomethyl)glycine of acceptable purity for use in formulation of herbicidal compositions. Typically, N-(phosphonomethyl)glycine wet-cake of acceptable purity contains at least about 95% by weight N-(phosphonomethyl)glycine product (dry basis) and the remainder is impurities such as reaction by-products, unreacted starting materials and impurities present in the starting materials. Individual impurities may have individual concentration specifications.

Without being held to a particular theory, it has been discovered that by separating a plurality of wet-cake products having different solids contents, different impurity concentrations, and/or different crystal size distributions from one or more product slurries comprising a precipitated product and impurities, the impurity content of the wet-cake products can be more effectively managed, thereby providing increased process flexibility. The process of the present invention is particularly advantageous for the concentration and recovery of crystalline products in processes wherein a conventional cake-washing step is either undesirable or insufficient to produce products of acceptable purity. For example, the process of the present invention has been discovered to be effective for producing wet-cake products of acceptable purity even when the product crystals precipitated from solution contain occluded impurities or impurities incorporated in the solids by other means which cannot be removed efficiently or practically by conventional cake washing or by other measures such as reslurrying with water or recrystallization. Further, the improved process of the present invention may also allow for the preparation of wet-cake products exhibiting improved packaging and handling characteristics.

It is important to note that the strategies set forth herein have wide application in processes for preparing reaction solutions comprising products subject to crystallization and concentrating and recovering crystallized product wet-cakes from the reaction solutions. The present invention has particular application in the concentration and recovery of wet-cake products from oxidation reaction solutions containing N-(phosphonomethyl)glycine product susceptible to crystallization and especially those containing N-(phosphonomethyl)glycine, wherein the oxidation reaction solution is produced by the catalytic liquid phase oxidation of an N-(phosphonomethyl)iminodiacetic acid substrate. However, it should be understood that the present invention is equally applicable to recovering wet-cake products from solutions containing N-(phosphonomethyl)glycine product produced by routes other than catalytic liquid phase oxidation of an N-(phosphonomethyl)iminodiacetic acid substrate that are well known to those skilled in the art.

As is recognized in the art, the liquid phase oxidation of N-(phosphonomethyl)iminodiacetic acid substrates may be carried out in a batch, semi-batch or continuous reactor system containing one or more oxidation reaction zones. The oxidation reaction zone(s) may be suitably provided by various reactor configurations, including those that have back-mixed characteristics, in the liquid phase and optionally in the gas phase as well, and those that have plug flow characteristics. Suitable reactor configurations having back-mixed characteristics include, for example, stirred tank reactors, ejector nozzle loop reactors (also known as venturi-loop reactors) and fluidized bed reactors. Suitable reactor configurations having plug flow characteristics include those having a packed or fixed catalyst bed (e.g., trickle bed reactors and packed bubble column reactors) and bubble slurry column reactors. Fluidized bed reactors may also be operated in a manner exhibiting plug flow characteristics. The configuration of the oxidation reactor system, including the number of oxidation reaction zones and the oxidation reaction conditions are not critical to the practice of the present invention. Suitable oxidation reactor systems and oxidation reaction conditions for liquid phase catalytic oxidation of an N-(phosphonomethyl)iminodiacetic acid substrate are well-known in the art and described, for example, by Ebner et al., U.S. Pat. No. 6,417,133, by Leiber et al., U.S. Pat. No. 6,586,621, and by Haupfear et al., International Publication No. WO 01/92272 and corresponding U.S. Publication No. US-2002-0068836-A1, the entire disclosures of which are incorporated herein by reference.

The process described herein has been found to be particularly useful in recovering multiple N-(phosphonomethyl)glycine wet-cake products from oxidation reaction solutions produced by various continuous oxidation reactor systems described, for example, by Haupfear et al. in International Publication No. WO 01/92272. However, it is important to note that the present invention is not limited to such applications or to use in conjunction with continuous oxidation reactor systems generally. As will be apparent to those skilled in the art, the strategies set forth herein may be advantageously applied in recovering crystalline wet-cake products from oxidation reaction solutions produced in a wide variety of reactor systems, including batch reactor systems.

Generally, in one embodiment, the process of the present invention comprises recovering separate wet-cake products from a slurry comprising precipitated product crystals and a mother liquor. The product slurry is divided into plural fractions comprising at least a first fraction and a second fraction. Product crystals are separated from each of the first and second fractions by dewatering in one or more liquid/solids separation devices to produce a first wet-cake product and a second wet-cake product, respectively.

More particularly, it has been found that the impurity content of a separated wet-cake product may be maintained below a desired value by generating at least two wet-cake products from a slurry comprising precipitated product crystals and a mother liquor such that the solids content of the second wet-cake product is greater than the solids content of the first wet-cake product. Thus, it is necessary in practicing this aspect of the present invention for the first and second wet-cake products to have different solids contents resulting in each wet-cake product having a different impurity composition due to the different amounts of impurity-containing mother liquor in the wet-cake. For example, the ratio of the solids content of the second wet-cake product to the solids content of the first wet-cake product, as measured by weight percent of solids in each of the first and second wet-cake products, is typically at least about 1.1. Preferably, the ratio of the solids content of the second wet-cake product to the solids content of the first wet-cake product, as measured by weight percent of solids in each of the first and second wet-cake products, is at least about 1.2. More preferably, the ratio of the solids content of the second wet-cake product to the solids content of the first wet-cake product, as measured by weight percent of solids in each of the first and second wet-cake products, is at least about 1.25.

In accordance with a preferred embodiment, the solids content of the second wet-cake product is preferably at least about 85% by weight solids. More preferably, the second wet-cake product has a solids content of from about 90% by weight solids to about 99% by weight solids. Most preferably, the second wet-cake product has a solids content of from about 95% by weight solids to about 99% by weight solids. Generally, increasing the solids content of the second wet-cake product allows the recovery of a greater quantity of the second wet-cake product of acceptable purity. Likewise, it is preferred that the first wet-cake product has a solids content of less than about 85% by weight solids. More preferably, the first wet-cake product has a solids content of less than about 75% by weight solids. For example, the first wet-cake product may have a solids content of from about 70% by weight solids to about 85% by weight solids. It should be understood that as impurity levels in the crystallization feed solution are reduced, product crystal size tends to increase, resulting in more efficient dewatering and higher solids content in the wet-cake products.

While not necessary or critical to the invention, it is contemplated that the first and second wet-cake products may typically be produced using separate liquid/solids separation devices, preferably separate liquid/solids separation devices arranged or operated in parallel. Generally, any liquid/solids separation device suitable for separating a crystal product from a mother liquor may be used in the present invention. However, because of the relatively high throughput and capacity requirements required by processes for the concentration and recovery of N-(phosphonomethyl)glycine products from a reaction solution resulting from the liquid phase oxidation of N-(phosphonomethyl)iminodiacetic acid substrates, preferred embodiments of the present invention typically employ liquid/solids separation devices adapted for pressure filtration, vacuum filtration, and/or centrifugation. For example, preferred liquid/solids separation devices may include vacuum drums, vacuum table filters and/or centrifuges. In a particularly preferred embodiment, product crystals are separated from the first and second slurry fractions by centrifugation, preferably in separate centrifuges, and even more preferably in separate centrifuges operated in parallel. In an especially preferred embodiment, the first wet-cake product is separated in a solid bowl centrifuge and the second wet-cake product is separated in a basket centrifuge (or a bank of basket centrifuges). Alternatively, it is contemplated that product crystals may be separated from the first and second slurry fractions in similar liquid/solids separation devices and/or under conditions such that the wet-cakes as initially produced have relatively equal solids contents. In such an embodiment, it may be possible to obtain the required solids content ratio within the first and second wet-cake products by combining the wet-cake product with mother liquor separated from either of the first or second product slurry fractions (i.e., by sending forward separated mother liquor for combination with the wet-cake product either directly or in a subsequent processing step).

A particularly preferred embodiment wherein product crystals are separated from first and second fractions of the product slurry in separate liquid/solids separation devices operated in parallel is illustrated in FIG. 1. A feed solution 1 comprising a product subject to crystallization is introduced into a crystallization stage 3 to produce a crystalline product slurry or magma 5 comprising precipitated product crystals and a mother liquor. For example, a product slurry comprising N-(phosphonomethyl)glycine product crystals and mother liquor may be produced by steam-driven evaporative crystallization, adiabatic crystallization or adiabatic crystallization with decantation of a reaction solution resulting from the catalytic liquid phase oxidation of an N-(phosphonomethyl)iminodiacetic acid substrate. An overhead vapor stream 7 is removed from the crystallization stage.

The product slurry 5 is divided into a first fraction 9 and a second fraction 11. The proportion of the product slurry divided into the first and second fractions may vary considerably. For example, first fraction 9 divided from slurry 5 may constitute from about 20% to about 100%, from about 40% to about 60%, or about 50% of the slurry and the second fraction 11 constitute the remainder of the slurry.

The first slurry fraction 9 is introduced into a first liquid/solids separation device 13 such as a centrifuge, preferably a solid bowl centrifuge, to produce a first wet-cake product 15 and a solids-depleted stream 17 (e.g., centrate) that is typically recycled back to the crystallization stage 3. However, at least a portion of the solids-depleted stream 17 can optionally be mixed back in with the wet-cake 15 as shown by the dashed line in FIG. 1, to generate a first wet-cake product of even lower solids content. Furthermore, at least a portion of the solids-depleted stream 17 can optionally be mixed back in with the wet-cake 15 in a later processing step.

The second product slurry fraction 11 can optionally be introduced into a hydroclone (or bank of hydroclones) 19 to form a concentrated second slurry fraction 23 enriched in precipitated product and a solids-depleted stream 21. The concentrated second fraction 23 is introduced into a separator feed tank 25 that feeds a second liquid/solids separation device, preferably a basket centrifuge. Alternatively, product slurry fraction 11 can be fed directly into the separator feed tank 25 or directly into the second liquid/solids separation device. In the preferred embodiment shown in FIG. 1, the concentrated second fraction is introduced into a bank of basket centrifuges. Thus, the concentrated second fraction 23 accumulated in the separator feed tank 25 is divided into concentrated slurry fractions 27A and 27B that are introduced into basket centrifuges 29A and 29B, respectively. The basket centrifuges produce a wet-cake product 31A and 31B, respectively, and these are combined to form a second wet-cake product 35. The basket centrifuges further produce centrates 33A and 33B that are further depleted in precipitated product and may be recycled back to the crystallization stage 3. However, at least a portion of centrates 33A and/or 33B can optionally be mixed back in with wet-cake products 31A, 31B and/or second wet-cake product 35 or mixed with first wet-cake product 15 to generate wet-cake products of even lower solids content.

As noted above, the liquid/solids separation devices used to dewater first and second product slurry fractions 9 and 11 in FIG. 1 are preferably a solid bowl centrifuge and one or more basket centrifuges, respectively. Where the first wet-cake product can contain more water and impurities without compromising the product specification, the use of a solid bowl centrifuge in conjunction with vertical basket centrifuges provides a higher solid capacity capability while requiring lower capital and operating costs.

In the embodiment shown in FIG. 1, the second wet-cake product 35 would have a lower impurity level than the first wet-cake product 15 due to the lower amount of entrained mother liquor in the wet-cake product. Furthermore, the second wet-cake product 35 typically has an impurity level below the required specification and an N-(phosphonomethyl)glycine product assay of at least about 95% by weight on a dry basis such that it can be packaged as a final product or used as feedstock in a subsequent processing step, for example, in the preparation of concentrated liquid or solid salts of N-(phosphonomethyl)glycine for use in formulation of herbicidal compositions. The first wet-cake product 15 as obtained may or may not meet the applicable purity specification, but can be utilized in conjunction with further processing (e.g., mixing with higher purity N-(phosphonomethyl)glycine product or recrystallization) to also produce a material or product of acceptable purity having different properties than the second wet-cake product.

The embodiment shown in FIG. 1 can be part of a process where stage 3 is the only crystallization step in the process However, the embodiment shown in FIG. 1 can also be part of a broader process that contains other crystallization stages, as described below in connection with FIG. 2.

In a particularly preferred embodiment, the present invention involves producing and recovering multiple wet-cakes containing crystalline N-(phosphonomethyl)glycine product from an oxidation reaction solution comprising N-(phosphonomethyl)glycine product and impurities in a process utilizing at least two crystallization stages operating in a semi-parallel manner.

Figure 2:
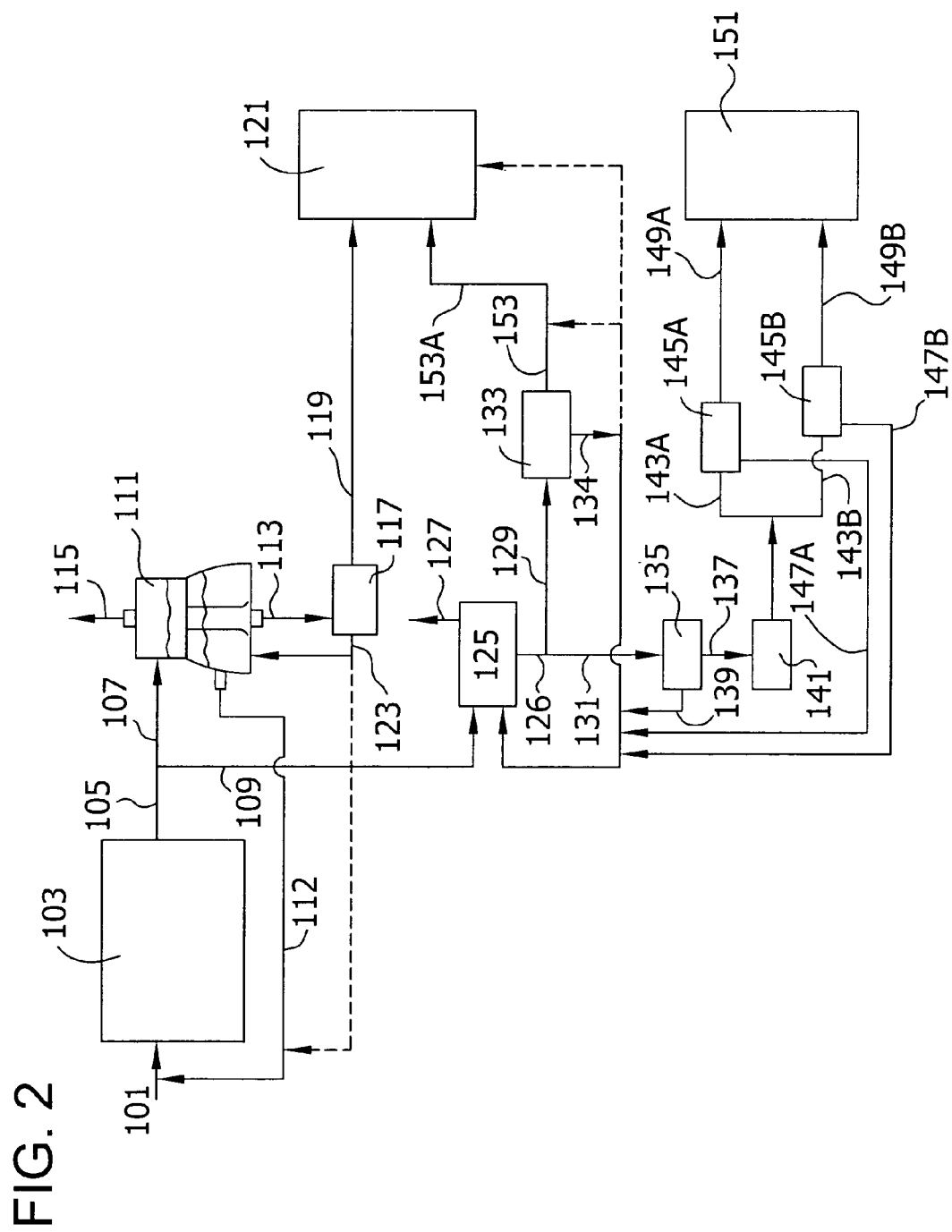
FIG. 2 is a schematic flow sheet of an integrated process for oxidizing an N-(phosphonomethyl)iminodiacetic acid substrate in a reactor system to form an oxidation reaction solution comprising an N-(phosphonomethyl)glycine product and for recovering two crystalline N-(phosphonomethyl) glycine wet-cake products from the oxidation reaction solution using a first adiabatic and a second non-adiabatic evaporative crystallization stages and separate liquid/solids separation systems or devices in parallel.

Referring now to FIG. 2, an aqueous feed stream 101 comprising an N-(phosphonomethyl)iminodiacetic acid substrate is introduced along with oxygen into an oxidation reactor system 103 comprising one or more oxidation reaction zone(s), wherein the N-(phosphonomethyl)iminodiacetic acid substrate is oxidatively cleaved in the presence of a suitable catalyst to form an aqueous oxidation reaction solution 105 comprising N-(phosphonomethyl)glycine product and impurities. In order to reduce the impurity level in the oxidation reaction solution 105, the catalyst employed in the oxidation reaction zone(s) is preferably a heterogeneous catalyst comprising a noble metal on a carbon support, for example, as described by Ebner et al., U.S. Pat. No. 6,417,133. The oxidation reaction solution 105 withdrawn from reactor system 103 is then divided into plural fractions and a portion 107 (i.e., a primary fraction of the oxidation reaction solution) is introduced and concentrated in a first crystallizer 111 that operates substantially adiabatically (i.e., any heat input or removal to the crystallizer is no greater than about 200 kcal/kg of oxidation reaction solution fed to the crystallizer) to produce a primary product slurry or magma 113 comprising precipitated N-(phosphonomethyl)glycine product crystals and primary mother liquor. Another portion 109 (i.e., a secondary fraction of the oxidation reaction solution) is introduced and concentrated in a non-adiabatic heat-driven evaporative crystallizer 125 to produce an evaporative crystallization slurry or magma 126 (i.e., a secondary product slurry) comprising precipitated N-(phosphonomethyl)glycine product crystals and secondary mother liquor.

Suitable operation of adiabatic crystallizer 111 and non-adiabatic crystallizer 125 in the product recovery system shown in FIG. 2 is generally described by Haupfear et al. in International Publication No. WO 01/92272 and corresponding U.S. Publication No. US-2002-0068836-A1, which are incorporated herein by reference. As described in this publication, adiabatic crystallizer 111 provides three different functions, including: flash vaporization of a fraction of the oxidation reaction solution, crystallization of N-(phosphonomethyl)glycine product by the cooling induced by the vacuum operation of the crystallizer, and subsequent decantation of a large portion of the crystallization mother liquor for recycle to the reactor system. This decantation also serves to concentrate the solids content of the primary product slurry fed to the liquid/solids separation device for reduced dewatering load and increased dewatering capacity. These functions can be provided integrally in single adiabatic crystallizer apparatus, or in a combination of apparatus.

Preferably, from about 30% to about 85%, more preferably from about 50% to about 80%, and even more preferably from about 65% to about 75% of the oxidation reaction solution 105 is introduced into the adiabatic crystallizer 111 via stream 107 as the primary fraction, while the remaining portion is introduced into the non-adiabatic heat-driven crystallizer 125 via stream 109 as the secondary fraction. The weight ratio of the secondary fraction 109 to the N-(phosphonomethyl)iminodiacetic acid substrate fed into the reactor system 103 is preferably from about 0.1 to about 9, more preferably from about 0.2 to about 5, even more preferably from about 0.25 to about 2.5. However, the proportion of the oxidation reaction solution 105 introduced into the adiabatic crystallizer 111 and the weight ratio of the secondary fraction 109 to the N-(phosphonomethyl)iminodiacetic acid substrate fed into the reactor system 103 are not narrowly critical in the practice of the present invention.

Operation of the adiabatic crystallizer 111 produces vapor 115 (i.e., the adiabatic crystallizer overhead) discharged from the top of the crystallizer, a decantate (i.e., primary mother liquor) stream 112 withdrawn from the crystallizer and the primary crystallization product slurry 113 removed from the bottom of the crystallizer and comprising precipitated crystalline N-(phosphonomethyl)glycine product and primary mother liquor containing uncrystallized (i.e., dissolved) N-(phosphonomethyl)glycine product and impurities. Preferably, at least a portion (and more preferably all) of the adiabatic crystallizer overhead 115 and/or decantate 112 withdrawn from the adiabatic crystallizer 111 is/are recycled back to the oxidation reactor system 103.

The primary crystallization product slurry 113 comprising precipitated crystalline N-(phosphonomethyl)glycine product and primary mother liquor removed from the bottom of the adiabatic crystallizer 111 is introduced into a liquid/solids separation device 117, preferably a basket centrifuge or bank of basket centrifuges, to produce a wet-cake product 119 and a solids-depleted stream 123 (e.g., centrate). At least a portion of the solids-depleted stream 123 may be recycled back to the adiabatic crystallizer 111 and/or optionally may be recycled back to the oxidation reactor system 103 as shown by the dashed line in FIG. 2. Preferably, the wet-cake product 119 has a solids content of from about 90% to about 99% by weight as described above.

The feed to the non-adiabatic crystallizer (i.e., secondary fraction 109) can be processed in a manner similar to that described above for feed solution 1 in FIG. 1. In the operation of the non-adiabatic evaporative crystallizer 125, heat is transferred to secondary fraction 109 to vaporize water (and small molecule impurities, such as formaldehyde and formic acid) and form a non-adiabatic crystallizer overhead vapor stream 127. The N-(phosphonomethyl)glycine product precipitates to produce the evaporative crystallization slurry 126 comprising precipitated N-(phosphonomethyl)glycine product and secondary mother liquor containing dissolved N-(phosphonomethyl)glycine product and impurities. Slurry 126 is withdrawn from the non-adiabatic evaporative crystallizer 125, and divided into plural fractions comprising a first fraction 129 and a second fraction 131. First fraction 129 is introduced into a first liquid/solids separation device 133, preferably a solid bowl centrifuge, to produce a first fraction wet-cake product 153 having a solids content of from about 70% to about 85% by weight as described above and a solids-depleted stream 134 (e.g., centrate). The solids-depleted stream 134 is typically recycled back to the non-adiabatic evaporative crystallizer 125. However, at least a portion of the solids-depleted stream 134 can optionally be mixed back with the wet-cake as shown by the dashed line in FIG. 2 to generate a first fraction wet-cake product 153A of even lower solids content. The first fraction wet-cake product 153 or 153A is then preferably blended with the wet-cake product 119 produced from the adiabatic crystallizer 111 to produce first wet-cake product 121. However, it should be understood that first fraction wet-cake product 153 or 153A and wet-cake product 119 may be individually subjected to further processing without first combining these materials to produce first wet-cake product 121. Furthermore, at least a portion of the solids-depleted stream 134 can optionally be blended with the first fraction wet-cake product 153 and the wet-cake product 119 produced from the adiabatic crystallizer 111 to produce first wet-cake product 121 as shown by the dashed line in FIG. 2.

The second fraction 131 of the evaporative product slurry is optionally introduced into a hydroclone (or bank of hydroclones) 135 to form a concentrated second slurry fraction 137 enriched in precipitated N-(phosphonomethyl) glycine product and a solids-depleted stream 139. The hydroclone solids-depleted stream 139 is preferably recycled back to the heat-driven evaporative crystallizer 125 for further recovery of the N-(phosphonomethyl)glycine product. The concentrated second fraction 137 is introduced into a separator feed tank 141, which feeds a second liquid/solids separation device, preferably a basket centrifuge capable of producing a wet-cake product having a relatively high solids content (typically from at least about 85% to about 99% by weight solids). Alternatively, the second fraction 131 of the evaporative product slurry can be fed directly into the separator feed tank 141 or directly into the second liquid/solids separation device. In the preferred embodiment shown in FIG. 2, the concentrated second slurry fraction 137 is introduced into a bank of basket centrifuges operated in parallel. Thus, the concentrated slurry accumulated in the separator feed tank 141 is divided into concentrated slurry fractions 143A and 143B that are introduced into basket centrifuges 145A and 145B, respectively. The basket centrifuges each produce a product wet-cake 149A and 149B, respectively, that are combined to form a second wet-cake product 151. The basket centrifuges also produce centrates 147A and 147B that are further depleted in precipitated product and may be recycled back to the non-adiabatic evaporative crystallizer 125. Alternatively, if necessary to obtain a wet-cake product of acceptable purity, at least a portion of centrates 147A, 147B and/or 134 may be purged from the process. It should be understood that as described herein, a bank of liquid/solids separation devises are considered to be operated in parallel even though the batch dewatering cycle in individual devises may not be in phase.

In operation of the product recovery system shown in FIG. 2, it will be expected that the impurity concentration in the primary mother liquor generated in the adiabatic crystallizer system will be lower than the impurity concentration in the secondary mother liquor generated in the non-adiabatic evaporative crystallizer system, particularly because the ratio of overheads to feed for the non-adiabatic crystallizer is significantly larger than the ratio of overhead to feed for the adiabatic crystallizer. It is also expected that the second wet-cake product 151, because of the lower amount of entrained mother liquor, will typically have an impurity level that meets specification and contains at least about 95% by weight N-phosphonomethyl)glycine product dry basis. However, first fraction wet-cake product 153, without further processing, may not be of acceptable purity due to the increased amount of entrained mother liquor. By combining first fraction wet-cake product 153 with wet-cake product 119 (generally a higher purity material), the overall ratio of impurity to N-(phosphonomethyl)glycine can be made acceptable, and thus further processing can generate a saleable product from this material. Such further processing may include drying to remove excess water to generate a wet-cake or further addition of base neutralization components to generate a suitable N-(phosphonomethyl)glycine salt product or formulation of acceptable purity. For example, the N-(phosphonomethyl)glycine product in the first wet-cake product 121, or in the first fraction wet-cake product 153 and wet-cake product 119 individually, may be neutralized with a base or bases in a conventional manner to prepare an agronomically acceptable salt of N-(phosphonomethyl)glycine as is commonly used in glyphosate herbicidal formulations. Examples of agronomically acceptable salts of N-(phosphonomethyl)glycine contain a cation selected from alkali metal cations (e.g., potassium and sodium ions), ammonium ion, isopropyl ammonium ion, tetra-alkylammonium ion, trialkyl sulfonium ion, protonated primary amine, protonated secondary amine and protonated tertiary amine. Thus, the embodiment shown in FIG. 2 can readily generate at least two distinct products of acceptable purity, second wet-cake product 151 and a product resulting from further processing of first wet-cake product 121 and provide overall improved process flexibility.

Although the embodiment shown in FIG. 2 utilizing two or more crystallization operations operated in semi-parallel has been found to be advantageous for producing a plurality of acceptable wet-cake products, depending on the incoming impurity levels in the oxidation reaction solution 105 or the fraction of second wet-cake product 151 produced from the non-adiabatic crystallizer, there may be a limit to the amount of second wet-cake product 151 having acceptable purity that can be made. In some instances, conventional washing of the second wet-cake product 151 can be used to reduce impurity concentrations and increase the amount of acceptable material 151 produced. However, in some instances described below, there are practical limits to the amount of cake washing that can be employed.

As the relative production of second wet-cake product 151 increases, impurities tend to accumulate in the secondary mother liquor of the non-adiabatic crystallizer system to a point where concentrations are sufficiently high to significantly undermine washing efficiency. Increased impurity concentrations tend to decrease crystal size such that subsequent dewatering operations are hampered and significant quantities of impurity-containing liquid remain entrained in second wet-cake product 151. Furthermore, it is believed that at higher concentrations, some of these impurities may become incorporated into the product crystals, decreasing cake-washing efficiency. These "solid phase occluded impurities" or other difficult to remove impurities in second wet-cake product 151 may require extensive washing of the crystals or other rigorous measures such as reslurrying with water or recrystallization in order to meet typical product purity specifications. These washes are usually recycled back to the evaporative crystallizer 125 to minimize the loss of soluble product. Unfortunately, the washed impurities also recycle and concentrate in the evaporative crystallizer, exacerbating the solid phase impurity occlusion problem and can also concentrate corrosive compounds raising materials of construction concerns, and ultimately leading to centrate purges (e.g., 147A, 147B and/or 134). The impurities not purged in the centrate end up in second wet-cake product 151, resulting in a disproportionate impurity redistribution to this portion of the product. In any event, as the amount of wash water increases, it becomes impractical and cost prohibitive to evaporate the recycled washes in the evaporative crystallizer, nor can these washes be recycled to other operations in the process or purged from the process without raising other concerns with respect to product purity and overall process efficiency.

In accordance with a further embodiment of the present invention, it has been discovered that the limitations described above may be overcome, increased process flexibility obtained and better impurity management achieved if the wet-cake products produced are the result of blending material from one of the crystallization operations with material from the other crystallization operation and preferably when material is transferred from the adiabatic crystallizer system into the non-adiabatic crystallizer system. This increased process flexibility is particularly useful as higher fractions of the total production are directed to the production of second wet-cake product 151. More particularly, it has been found that impurities within the wet-cake products produced by the process of the present invention may be maintained below desired levels by: (i) net transfer of impurities contained in the first (i.e., primary) and/or second (i.e., secondary) mother liquor fractions to the other of the first (i.e., adiabatic) and second (i.e., non-adiabatic evaporative) crystallization operations; (ii) net transfer of impurities contained in the first and/or second mother liquor fractions to the other of the first and second liquid/solids separation steps associated with the other of the first and second crystallization operations; (iii) net transfer of wet-cake product of relatively low impurities content, as obtained from one of the first and second liquid/solids separation steps, to the other of the first and second crystallization operations; (iv) net transfer of wet-cake product of relatively low impurities content, as obtained from one of the first and second liquid/solids separation steps, to the other of the first and second liquid/solids separation steps associated with the other of the first and second crystallization operations; (v) net transfer of product slurry or magma of relatively low impurities content, as obtained in one of the first and second crystallization operations, to the other of the first and second crystallization operations; (vi) net transfer of product slurry or magma of relatively low impurities content, as obtained in one of the first and second crystallization operations, to the other of the first and second liquid/solids separation steps associated with the other of the first and second crystallization operations; or any combination of (i), (ii), (iii), (iv), (v) and/or (vi).

Figure 3:
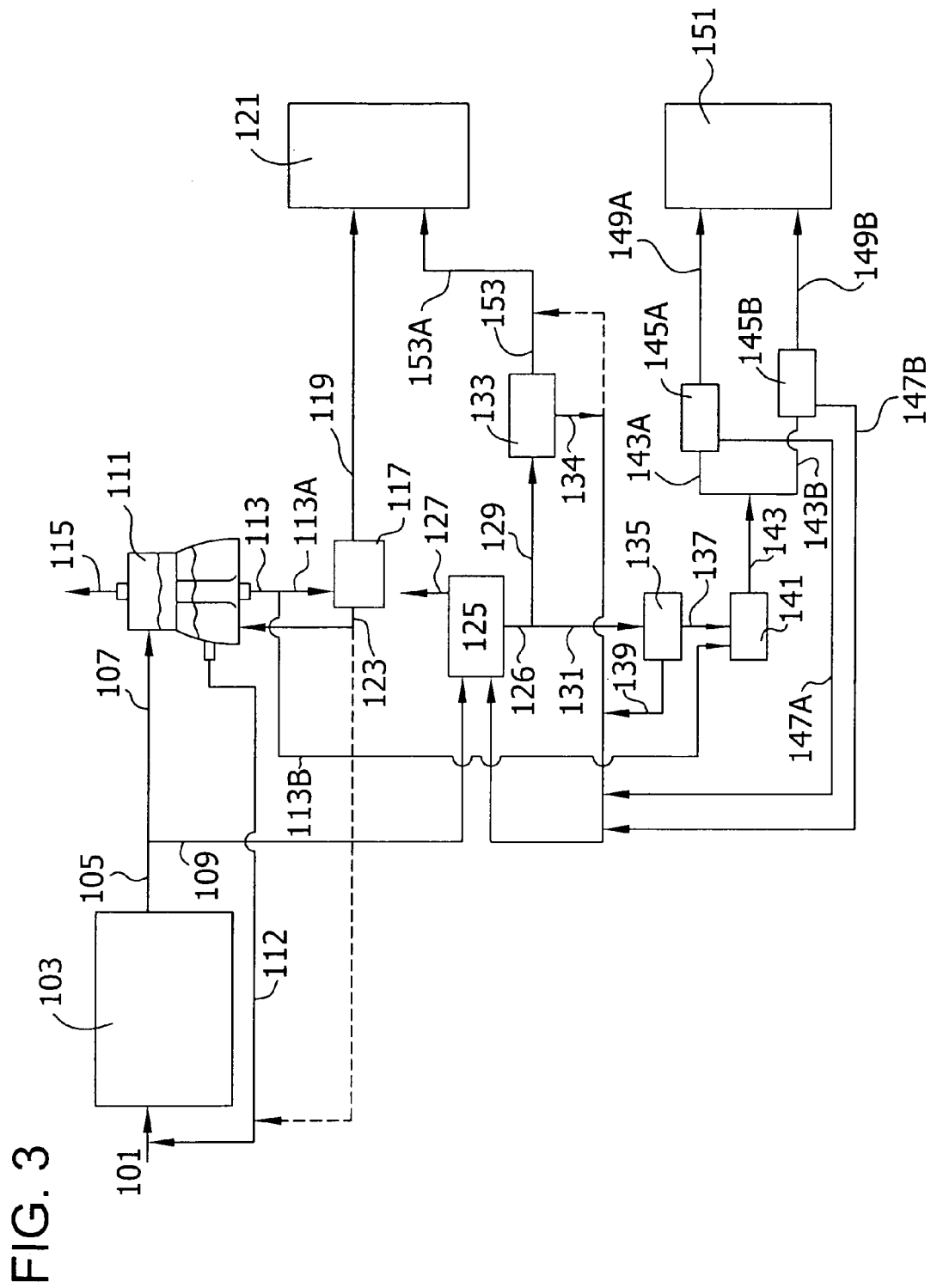
FIG. 3 is a schematic flow sheet of a process as described in FIG. 2 wherein impurity distribution among the crystalline N-(phosphonomethyl)glycine wet-cake products is managed by net transfer of product slurry or magma from a first adiabatic crystallization train to the product slurry of a second non-adiabatic evaporative crystallization train.

A preferred embodiment of the process of the present invention for producing and recovering two wet-cake products comprising crystalline N-(phosphonomethyl)glycine from an oxidation reaction solution comprising dissolved N-(phosphonomethyl)glycine product and impurities is shown in FIG. 3. Similar to the process shown and described in FIG. 2, the product recovery system of FIG. 3 employs a combination of an adiabatic crystallizer system and a non-adiabatic heat-driven evaporative crystallizer operated in semi-parallel. However, in accordance with this embodiment, impurity distribution among the crystalline N-(phosphonomethyl)glycine wet-cake products is managed by net transfer of primary product slurry or magma from the adiabatic crystallizer system and combining it with N-(phosphonomethyl)glycine product contained in the secondary fraction of the oxidation reaction solution. More particularly, in the embodiment illustrated in FIG. 3, impurity distribution among the crystalline N-(phosphonomethyl) glycine wet-cake products is managed by net transfer of primary product slurry to the secondary product slurry or magma of the evaporative crystallizer.

Many of the various streams shown in FIG. 3 are analogous to those described above with respect to FIG. 2. Referring now to FIG. 3, an aqueous feed stream 101 comprising an N-(phosphonomethyl)iminodiacetic acid substrate is introduced along with oxygen into an oxidation reactor system 103 comprising one or more oxidation reaction zone(s), wherein the N-(phosphonomethyl)iminodiacetic acid substrate is oxidatively cleaved in the presence of a catalyst to form an oxidation reaction solution 105. The oxidation reaction solution 105 withdrawn from the reactor system 103 is then divided into plural fractions and a portion 107 (i.e., a primary fraction of the oxidation reaction solution) is introduced into an adiabatic crystallizer 111 to produce a primary product slurry 113 comprising precipitated N-(phosphonomethyl)glycine product crystals and primary mother liquor. Another portion 109 (i.e., a secondary fraction of the oxidation reaction solution) is introduced into a non-adiabatic heat-driven evaporative crystallizer 125 to produce an evaporative crystallization slurry 126 (i.e., a secondary product slurry) comprising precipitated N-(phosphonomethyl)glycine product crystals and secondary mother liquor.

Operation of the adiabatic crystallizer 111 produces vapor 115 (i.e., the adiabatic crystallizer overhead) discharged from the top of the crystallizer, a decantate (i.e., primary mother liquor) stream 112 withdrawn from the crystallizer and a primary crystallization product slurry 113 removed from the bottom of the crystallizer and comprising precipitated crystalline N-(phosphonomethyl)glycine product and primary mother liquor. Preferably, at least a portion (and more preferably all) of the adiabatic crystallizer overhead 115 and/or decantate 112 withdrawn from the adiabatic crystallizer 111 is/are recycled back to the oxidation reactor system 103.

The primary crystallization product slurry 113 is divided into two portions 113A and 113B. Portion 113A is introduced into a liquid/solids separation device 117, preferably a basket centrifuge or bank of basket centrifuges, to produce a wet-cake product 119 and a solids-depleted stream 123 (e.g., centrate). At least a portion of the solids-depleted stream 123 may be recycled back to the adiabatic crystallizer 111 and/or optionally may be recycled back to the oxidation reactor system 103 as shown by the dashed line in FIG. 3. Preferably, the wet-cake product 119 has a solids content of from about 90% to about 99% by weight as described above. Portion 113B is transferred to separator feed tank 141 as described below.

In the operation of the non-adiabatic evaporative crystallizer 125, heat is transferred to secondary fraction 109 to vaporize water (and small molecule impurities, such as formaldehyde and formic acid) and form a non-adiabatic crystallizer overhead vapor stream 127. The N-(phosphonomethyl)glycine product precipitates to produce an evaporative crystallization slurry 126 comprising precipitated crystalline N-(phosphonomethyl)glycine product and secondary mother liquor. Slurry 126 is withdrawn from the non-adiabatic evaporative crystallizer 125, and divided into plural fractions comprising a first fraction 129 and a second fraction 131. First fraction 129 is introduced into a first liquid/solids separation device 133, preferably a solid bowl centrifuge, to produce a first fraction wet-cake product 153 having a solids content of from about 70% to about 85% by weight as described above and a solids-depleted stream 134 (e.g., centrate). The solids-depleted stream 134 is typically recycled back to the non-adiabatic evaporative crystallizer 125. However, at least a portion of the solids-depleted stream 134 can optionally be mixed back with the wet-cake as shown by the dashed line in FIG. 3 to generate a first fraction wet-cake product 153A of even lower solids content. The first fraction wet-cake product 153 or 153A is then preferably blended with the wet-cake product 119 produced from the adiabatic crystallizer 111 described above to produce first wet-cake product 121.

The second fraction 131 of the evaporative product slurry is optionally introduced into a hydroclone (or bank of hydroclones) 135 to form a concentrated second slurry fraction 137 enriched in precipitated N-(phosphonomethyl) glycine product and a solids-depleted stream 139. The hydroclone solids-depleted stream 139 is preferably recycled back to the heat-driven evaporative crystallizer 125 for further recovery of the N-(phosphonomethyl)glycine product. The concentrated second fraction 137 is introduced into a separator feed tank 141 and combined with portion 113B of the primary product slurry to form a secondary fraction product mixture 143. Secondary fraction product mixture 143 is fed to a liquid/solids separation device, preferably a basket centrifuge capable of producing a wet-cake product having a relatively high solids content (typically from at least about 85% to about 99% by weight solids). Alternatively, the second fraction 131 of the evaporative product slurry can be fed directly into the separator feed tank 141 or both the second fraction 131 of the evaporative product slurry and the portion 113B of the primary product slurry can be fed directly into the second liquid/solids separation device. In the preferred embodiment shown in FIG. 3, the secondary fraction product mixture 143 is introduced into a bank of basket centrifuges operated in parallel. Thus, the secondary fraction product mixture 143 from the separator feed tank 141 is divided into product mixture fractions 143A and 143B that are introduced into basket centrifuges 145A and 145B, respectively. The basket centrifuges each produce a product wet-cake 149A and 149B that are combined to form the second wet-cake product 151. The basket centrifuges further produce centrates 147A and 147B that are further depleted in precipitated product and may be recycled back to the non-adiabatic evaporative crystallizer 125. Alternatively, if necessary to obtain a wet-cake product of acceptable purity, at least a portion of centrates 147A, 147B and/or 134 may be purged from the process.

Operation of the embodiment shown in FIG. 3 is particularly advantageous to resolve the limitations on production of second wet-cake product 151 (relative to the total system production) imposed by the operation of the system shown in FIG. 2 when cake washing of second wet-cake product 151 becomes impractical. The solid and liquid phase impurities in the portion 113B of primary product slurry 113 are considerably lower than those in the concentrated second slurry fraction 137. The blending of these streams in 143 above a minimum ratio lowers the average impurity level in the solid and/or liquid phase, enabling a decrease and ultimately elimination of the water wash of second wet-cake product 151. The resulting second wet-cake product 151 may carry a greater quantity of impurities from the evaporative crystallizer than otherwise, resulting in a better balance of impurities between wet-cake products 121 and 151. This occurs in spite of the partial dilution of liquid phase impurities in second product fraction mixture 143 due to the lower impurity content in portion 113B of primary product slurry 113. In typical practice, advantageous results are achieved when from about 10% to about 30% by weight of the primary product slurry 113 is transferred to secondary fraction product mixture 143. However, it should be understood that the exact proportion can vary considerably without departing from the scope of the present invention and, as would be understood by those skilled in the art, is dependent upon a variety of parameters, including the composition of the secondary product slurry 126 from the evaporative crystallizer.

Figure 4:
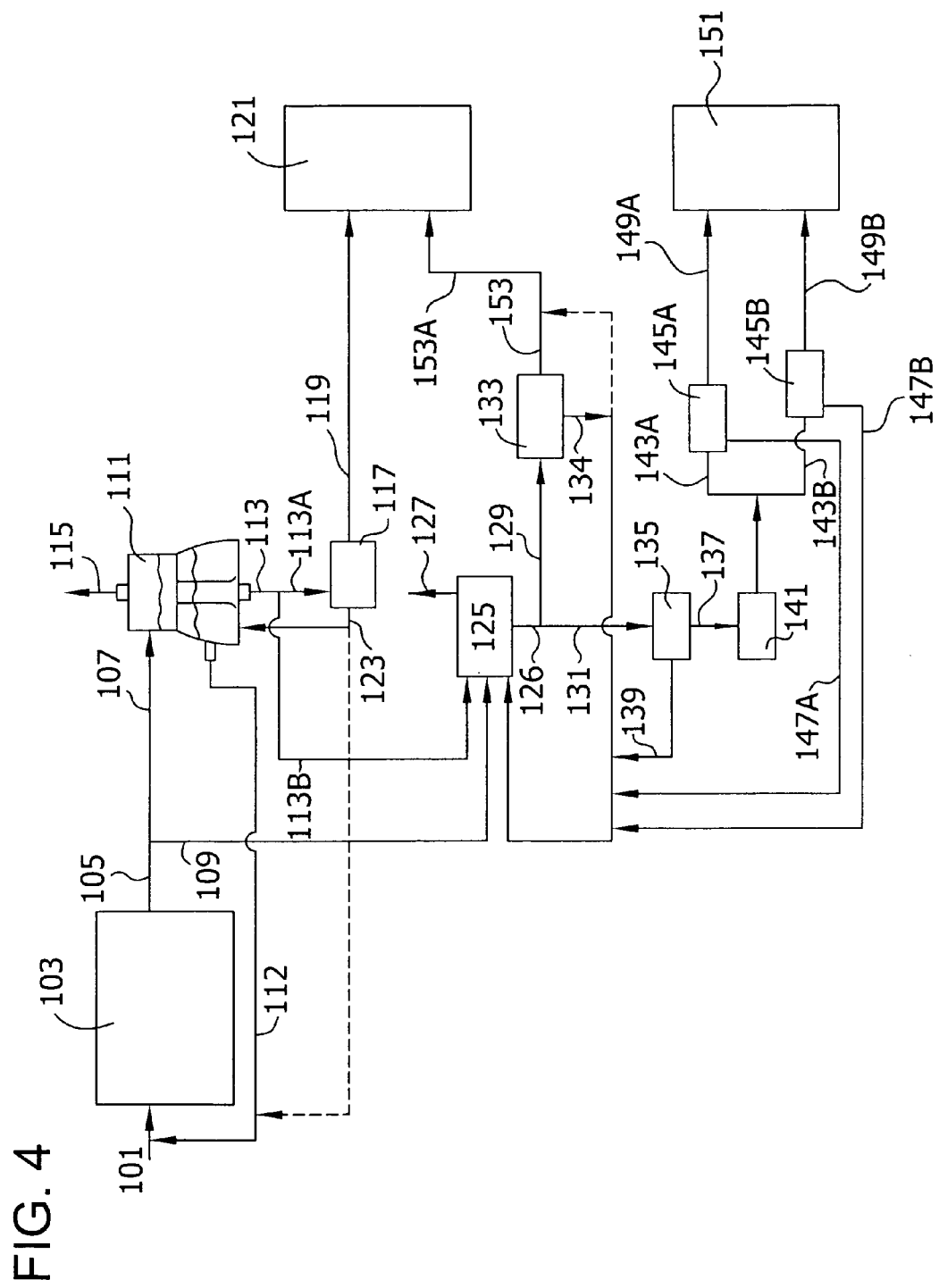
FIG. 4 is a schematic flow sheet of a process as described in FIG. 2 wherein impurity distribution among the crystalline N-(phosphonomethyl)glycine wet-cake products is managed by net transfer of product slurry from a first adiabatic crystallization train to a second non-adiabatic evaporative crystallization stage.
Figure 5:
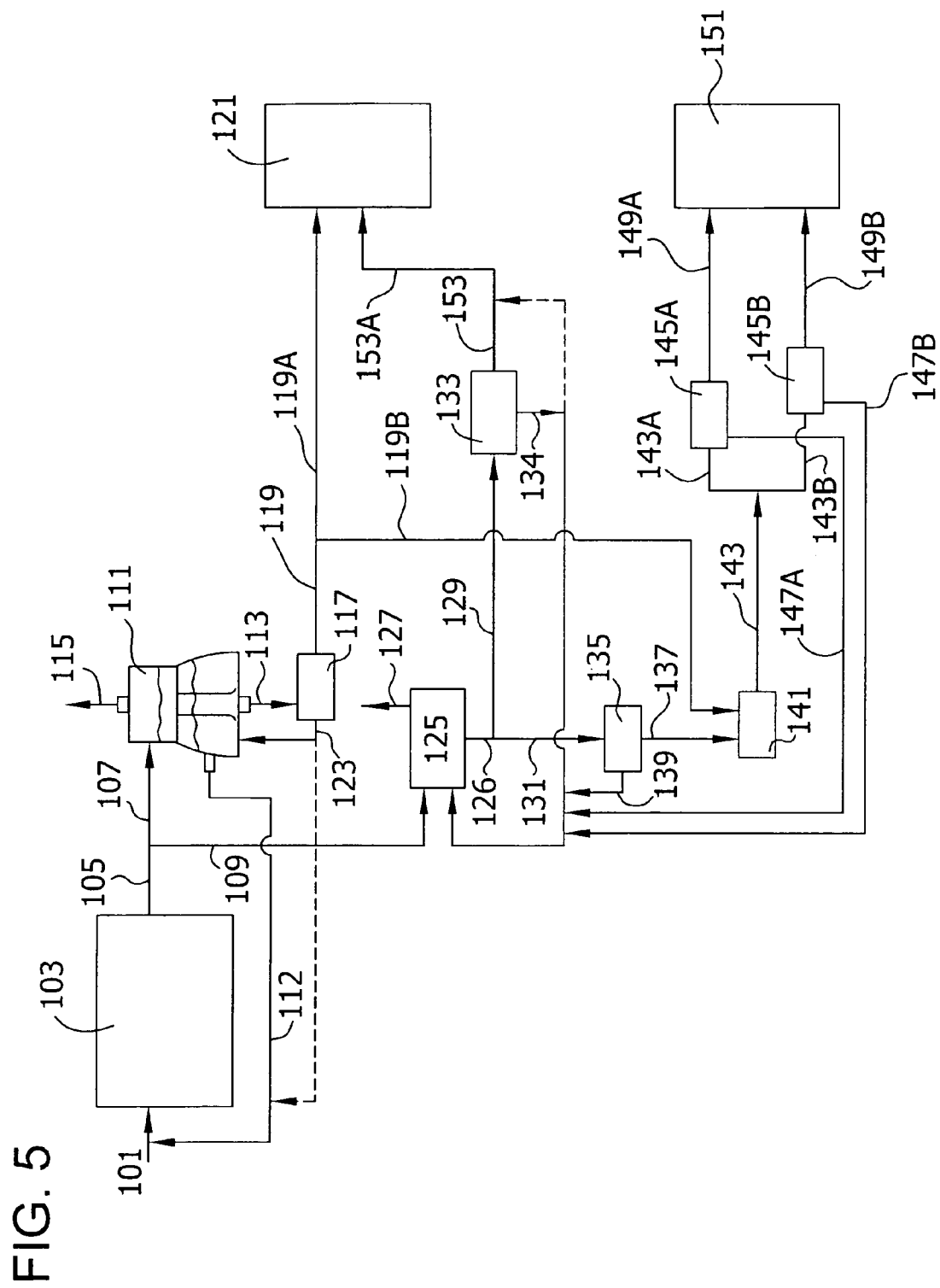
FIG. 5 is a schematic flow sheet of a process as described in FIG. 2 wherein impurity distribution among the crystalline N-(phosphonomethyl)glycine wet-cake products is managed by net transfer of N-(phosphonomethyl)glycine product crystals from a first adiabatic crystallization train to the product slurry of a second non-adiabatic evaporative crystallization train.
Figure 6:
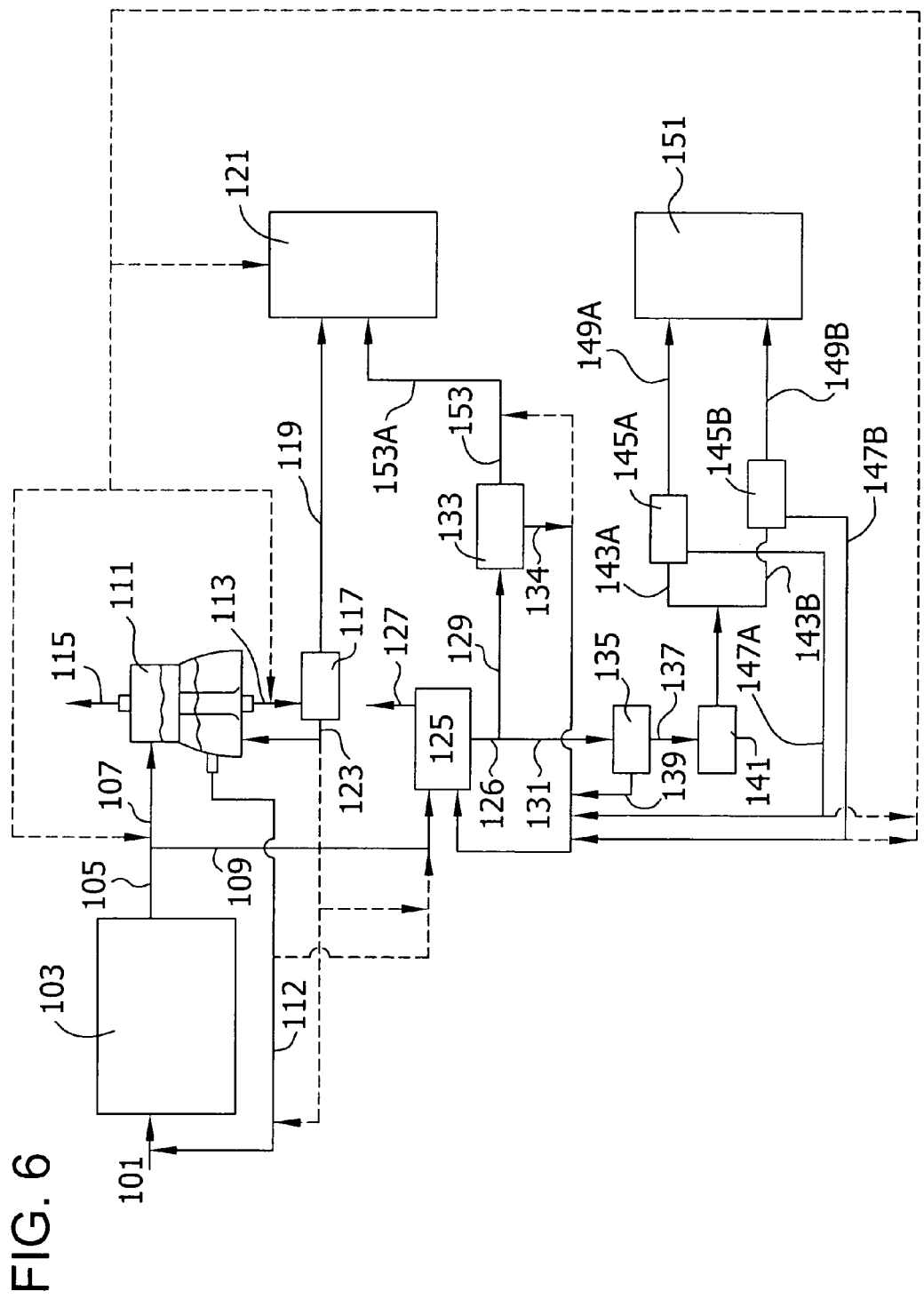
FIG. 6 is a schematic flow sheet of a process as described in FIG. 2 wherein impurity distribution among the crystalline N-(phosphonomethyl)glycine wet-cake products is managed by net transfer of impurities contained in mother liquor from a first adiabatic crystallization operation and/or a second non-adiabatic evaporative crystallization operation to: (i) the other of the adiabatic and/or evaporative crystallization operations; (ii) the other of the adiabatic and/or evaporative liquid/solids separation steps; (iii) the other of the adiabatic or evaporative wet-cake products; or any combination of (i), (ii) and/or (iii).

Other preferred embodiments for producing and recovering two wet-cake products comprising crystalline N-(phosphonomethyl)glycine from an oxidation reaction solution comprising dissolved N-(phosphonomethyl)glycine product and impurities are shown in FIGS. 4–6. Similar to the processes shown and described in FIGS. 2 and 3, the product recovery systems of these additional embodiments employ a combination of an adiabatic crystallizer system and a non-adiabatic heat-driven evaporative crystallizer operated in semi-parallel. Accordingly, many of the various streams shown in FIGS. 4–6 are analogous to those described above with respect to FIGS. 2 and 3.

The process embodiment illustrated in FIG. 4 is a variation of the process described in FIG. 3 in which impurity distribution among the crystalline N-(phosphonomethyl) glycine wet-cake products is likewise managed by net transfer of primary product slurry or magma from the adiabatic crystallizer system and combining it with N-(phosphonomethyl)glycine product contained in the secondary fraction of the oxidation reaction solution. However, in the process depicted in FIG. 4, impurity distribution among the crystalline N-(phosphonomethyl)glycine wet-cake products is managed by net transfer of primary product slurry or magma from the adiabatic crystallizer system to the evaporative crystallizer.

Referring now to FIG. 4, an aqueous feed stream 101 comprising an N-(phosphonomethyl)iminodiacetic acid substrate is introduced along with oxygen into an oxidation reactor system 103 comprising one or more oxidation reaction zone(s), wherein the N-(phosphonomethyl)iminodiacetic acid substrate is oxidatively cleaved in the presence of a catalyst to form an oxidation reaction solution 105. The oxidation reaction solution 105 withdrawn from the reactor system 103 is then divided into plural fractions and a portion 107 (i.e., a primary fraction of the oxidation reaction solution) is introduced into an adiabatic crystallizer 111 to produce a primary product slurry 113 comprising precipitated N-(phosphonomethyl)glycine product crystals and primary mother liquor. Another portion 109 (i.e., a secondary fraction of the oxidation reaction solution) is introduced into a non-adiabatic heat-driven evaporative crystallizer 125 to produce an evaporative crystallization slurry 126 (i.e., a secondary product slurry) comprising precipitated N-(phosphonomethyl)glycine product crystals and secondary mother liquor.

Operation of the adiabatic crystallizer 111 produces vapor 115 (i.e., the adiabatic crystallizer overhead) discharged from the top of the crystallizer, a decantate (i.e., primary mother liquor) stream 112 withdrawn from the crystallizer and a primary crystallization product slurry 113 removed from the bottom of the crystallizer and comprising precipitated crystalline N-(phosphonomethyl)glycine product and primary mother liquor. Preferably, at least a portion (and more preferably all) of the adiabatic crystallizer overhead 115 and/or decantate 112 withdrawn from the adiabatic crystallizer 111 is/are recycled back to the oxidation reactor system 103.

The primary crystallization product slurry 113 is divided into two portions 113A and 113B. Portion 113A is introduced into a liquid/solids separation device 117, preferably a basket centrifuge or bank of basket centrifuges, to produce a wet-cake product 119 and a solid-depleted stream 123 (e.g., centrate). At least a portion of the solids-depleted stream 123 may be recycled back to the adiabatic crystallizer 111 and/or optionally may be recycled back to the oxidation reactor system 103 as shown by the dashed line in FIG. 4. Preferably, the wet-cake product 119 has a solids content of from about 90% to about 99% by weight as described above.

Portion 113B of the primary product slurry 113 is combined with the secondary fraction 109 of the oxidation reaction solution to form an evaporative crystallizer feed mixture transferred to the evaporative crystallizer 125 for precipitation of crystalline N-(phosphonomethyl)glycine product. While not necessary or critical to the present invention, it is contemplated that portion 113B may be introduced directly into the evaporative crystallizer 125 or may be premixed with secondary fraction 109, for example, in a holding tank (not shown). In either case, heat is transferred to the resulting evaporative crystallizer feed mixture in the non-adiabatic evaporative crystallizer 125 to vaporize water (and small molecule impurities, such as formaldehyde and formic acid) and form a non-adiabatic crystallizer overhead vapor stream 127. The N-(phosphonomethyl)glycine product precipitates to produce an evaporative crystallization slurry 126 comprising precipitated crystalline N-(phosphonomethyl)glycine product and secondary mother liquor. Slurry 126 is withdrawn from the non-adiabatic evaporative crystallizer 125, and divided into plural fractions comprising a first fraction 129 and a second fraction 131. First fraction 129 is introduced into a first liquid/solids separation device 133, preferably a solid bowl centrifuge, to produce a first fraction wet-cake product 153 having a solids content of from about 70% to about 85% by weight as described above and a solids-depleted stream 134 (e.g., centrate). The solids-depleted stream 134 is typically recycled back to the non-adiabatic evaporative crystallizer 125. However, at least a portion of the solids-depleted stream 134 can optionally be mixed back with the wet-cake as shown by the dashed line in FIG. 4 to generate a first fraction wet-cake product 153A of even lower solids content. The first fraction wet-cake product 153 or 153A is then preferably blended with the wet-cake product 119 produced from the adiabatic crystallizer 111 described above to produce first wet-cake product 121.

The second fraction 131 of the evaporative product slurry is optionally introduced into a hydroclone (or bank of hydroclones) 135 to form a concentrated second slurry fraction 137 enriched in precipitated N-(phosphonomethyl)glycine product and a solids-depleted stream 139. The hydroclone solids-depleted stream 139 is preferably recycled back to the heat-driven evaporative crystallizer 125 for further recovery of the N-(phosphonomethyl)glycine product. The concentrated second fraction 137 is introduced into a separator feed tank 141, which feeds a second liquid/solids separation device, preferably a basket centrifuge capable of producing a wet-cake product having a relatively high solids content (typically from at least about 85% to about 99% by weight solids). Alternatively, the second fraction 131 of the evaporative product slurry can be fed directly into the separator feed tank 141 or directly into the second liquid/solids separation device. In the preferred embodiment shown in FIG. 4, the concentrated second slurry fraction 137 is introduced into a series of basket centrifuges operated in parallel. Thus, the concentrated slurry accumulated in the separator feed tank 141 is divided into concentrated slurry fractions 143A and 143B that are introduced into basket centrifuges 145A and 145B, respectively. The basket centrifuges each produce a product wet-cake 149A and 149B that are combined to form the second product wet-cake 151. The basket centrifuges further produce centrates 147A and 147B that are further depleted in precipitated product and may be recycled back to the non-adiabatic evaporative crystallizer 125. Alternatively, if necessary to obtain a wet-cake product of acceptable purity, at least a portion of centrates 147A, 147B and/or 134 may be purged from the process.

Without being bound to a particular theory, it is believed that transfer of the portion 113B of primary product slurry 113 to the evaporative crystallizer may advantageously affect the precipitation of N-(phosphonomethyl)glycine product crystals from secondary fraction 109 of the oxidation reaction solution such that less impurities and better crystal size distribution may be obtained. More particularly, portion 113B of the adiabatic primary product slurry typically contains large product crystals of high purity. Thus, transfer of portion 113B to the evaporative crystallizer may effectively "seed" the crystallizer to promote crystal growth such that less impurities may be incorporated in the crystal structure. In any case, one skilled in the art would understand that any crystal growth incorporating the relatively pure crystals from portion 113B will increase the overall purity profile of the product slurry produced from the evaporative crystallization operation.

In practice, the proportion of the primary product slurry 113 transferred to the non-adiabatic evaporative crystallizer 125 can vary considerably without departing from the scope of the present invention and advantageous results obtained.

Another preferred embodiment of the present invention for producing and recovering two wet-cake products comprising crystalline N-(phosphonomethyl)glycine product from an oxidation reaction solution comprising dissolved N-(phosphonomethyl)glycine and impurities is shown in FIG. 5. In accordance with this further embodiment, impurity distribution among the crystalline N-(phosphonomethyl)glycine wet-cake products is managed by net transfer of N-(phosphonomethyl)glycine product crystals contained in the first wet-cake product from the adiabatic crystallizer system and combining the crystals with N-(phosphonomethyl)glycine product contained in the secondary fraction of the oxidation reaction solution. More particularly, in the embodiment illustrated in FIG. 5, impurity distribution among the crystalline N-(phosphonomethyl)glycine wet-cake products is managed by net transfer of N-(phosphonomethyl)glycine product crystals from the first wet-cake product to the secondary product slurry or magma of the evaporative crystallizer.

Referring now to FIG. 5, an aqueous feed stream 101 comprising an N-(phosphonomethyl)iminodiacetic acid substrate is introduced along with oxygen into an oxidation reactor system 103 comprising one or more oxidation reaction zone(s), wherein the N-(phosphonomethyl)iminodiacetic acid substrate is oxidatively cleaved in the presence of a catalyst to form an oxidation reaction solution 105. The oxidation reaction solution 105 withdrawn from the reactor system 103 is then divided into plural fractions and a portion 107 (i.e., a primary fraction of the oxidation reaction solution) is introduced into an adiabatic crystallizer 111 to produce a primary product slurry 113 comprising precipitated N-(phosphonomethyl)glycine product crystals and primary mother liquor. Another portion 109 (i.e., a secondary fraction of the oxidation reaction solution) is introduced into a non-adiabatic heat-driven evaporative crystallizer 125 to produce an evaporative crystallization slurry 126 (i.e., a secondary product slurry) comprising precipitated N-(phosphonomethyl)glycine product crystals and secondary mother liquor.

Operation of the adiabatic crystallizer 111 produces vapor 115 (i.e., the adiabatic crystallizer overhead) discharged from the top of the crystallizer, a decantate (i.e., primary mother liquor) stream 112 withdrawn from the crystallizer and a primary crystallization product slurry 113 removed from the bottom of the crystallizer and comprising precipitated crystalline N-(phosphonomethyl)glycine product and primary mother liquor. Preferably, at least a portion (and more preferably all) of the adiabatic crystallizer overhead 115 and/or decantate 112 withdrawn from the adiabatic crystallizer 111 is/are recycled back to the oxidation reactor system 103.

The primary crystallization product slurry 113 comprising precipitated crystalline N-(phosphonomethyl)glycine product and primary mother liquor removed from the bottom of the crystallizer is introduced into a liquid/solids separation device 117, preferably a basket centrifuge or bank of basket centrifuges, to produce a primary wet-cake product 119 and a solids-depleted stream 123 (e.g., centrate). At least a portion of the solids-depleted stream 123 may be recycled back to the adiabatic crystallizer 111 and/or optionally may be recycled back to the oxidation reactor system as shown by the dashed line in FIG. 5. Preferably, the primary wet-cake product 119 has a solids content of from about 90% to about 99% by weight as described above. As further described below, at least a portion 119B of the primary wet-cake 119 is transferred to separator feed tank 141 for blending with the second fraction product slurry produced in the evaporative crystallization operation. Preferably, another portion 119A of the primary wet-cake 119 is reserved for inclusion in first wet-cake product 121.

In the operation of the non-adiabatic evaporative crystallizer, heat is transferred to secondary fraction 109 to vaporize water (and small molecule impurities, such as formaldehyde and formic acid) and form a non-adiabatic crystallizer overhead vapor stream 127. The N-(phosphonomethyl)glycine product precipitates to produce an evaporative crystallization slurry 126 comprising precipitated crystalline N-(phosphonomethyl)glycine product and secondary mother liquor. Slurry 126 is withdrawn from the non-adiabatic evaporative crystallizer 125, and divided into plural fractions comprising a first fraction 129 and a second fraction 131. First fraction 129 is introduced into a first liquid/solids separation device 133, preferably a solid bowl centrifuge, to produce a first fraction wet-cake product 153 having a solids content of from about 70% to about 85% by weight as described above and a solids-depleted stream 134 (e.g., centrate). The solids-depleted stream 134 is typically recycled back to the non-adiabatic evaporative crystallizer 125. However, at least a portion of the solids-depleted stream 134 can optionally be mixed back with the wet-cake as shown by the dashed line in FIG. 5 to generate a first fraction wet-cake product 153A of even lower solids content. The first fraction wet-cake product 153 or 153A is then preferably blended with portion 119A of the wet-cake product 119 produced from the adiabatic crystallizer 111 to produce first wet-cake product 121.

The second fraction 131 of the evaporative product slurry is optionally introduced into a hydroclone (or bank of hydroclones) 135 to form a concentrated second slurry fraction 137 enriched in precipitated N-(phosphonomethyl)glycine product and a solids-depleted stream 139. The hydroclone solids-depleted stream 139 is preferably recycled back to the heat-driven evaporative crystallizer 125 for further recovery of the N-(phosphonomethyl)glycine product. The concentrated second fraction 137 is introduced into a separator feed tank 141 and combined with portion 119B of the wet-cake produced in the adiabatic crystallization operation described above to form a secondary fraction product mixture 143. Secondary fraction product mixture 143 is fed into a second liquid/solids separation device, preferably a basket centrifuge capable of producing a wet-cake product having a relatively high solids content (typically from at least about 85% to about 99% by weight solids). Alternatively, the second fraction 131 of the evaporative product slurry can be fed directly into the separator feed tank 141 or both the second fraction 131 of the evaporative product slurry and the portion 119B of the wet-cake produced in the adiabatic crystallization operation can be fed directly into the second liquid/solids separation device. In the preferred embodiment shown in FIG. 5, the secondary fraction product mixture 143 is introduced into a bank of basket centrifuges operated in parallel. Thus, the secondary fraction product mixture 143 from the separator feed tank 141 is divided into product mixture fractions 143A and 143B that are introduced into basket centrifuges 145A and 145B, respectively. The basket centrifuges each produce a product wet-cake 149A and 149B that are combined to form the second wet-cake product 151. The basket centrifuges further produce centrates 147A and 147B that are further depleted in precipitated product and may be recycled back to the non-adiabatic evaporative crystallizer 125. Alternatively, if necessary to obtain a wet-cake product of acceptable purity, at least a portion of centrates 147A, 147B and/or 134 may be purged from the process.

As compared to FIG. 3, the blending of adiabatic wet-cake in secondary fraction product mixture 143 instead of adiabatic slurry allows a higher level of liquid phase impurities to be carried by the combined solids stream, resulting in an improvement in impurity distribution away from first wet-cake product 121. This scheme also reduces the evaporation load in the evaporative crystallizer 125 by the reduction in water flowing into the evaporative crystallizer system.

In a further process embodiment of the present invention in which impurity distribution among the crystalline N-(phosphonomethyl)glycine wet-cake products is managed by net transfer of N-(phosphonomethyl)glycine product crystals contained in the first wet-cake product from the adiabatic crystallizer system and combining the crystals with N-(phosphonomethyl)glycine product contained in the secondary fraction of the oxidation reaction solution, the process illustrated in FIG. 5 is modified such that N-(phosphonomethyl)glycine product crystals from the first wet-cake product are transferred to the evaporative crystallizer. That is, portion 119B of the primary wet-cake 119 is combined with the secondary fraction 109 of the oxidation reaction solution to form an evaporative crystallizer feed mixture transferred to the evaporative crystallizer 125 for precipitation of crystalline N-(phosphonomethyl)glycine product. While not necessary or critical to the present invention, it is contemplated that portion 119B may be introduced directly into the evaporative crystallizer 125 or may be premixed with secondary fraction 109, for example, in a holding tank.

In practice, the proportion of the adiabatic wet-cake 119 transferred to secondary fraction product mixture 143 and/or to the evaporative crystallizer 125 can vary considerably without departing from the scope of the present invention and advantageous results obtained.

In a still further alternative embodiment of the process illustrated in FIG. 5, rather than blending adiabatic wet-cake 119B in secondary fraction product mixture 143 and/or introducing it into the evaporative crystallizer 125, adiabatic wet-cake may be combined and physically mixed directly with the second wet-cake product 151 to obtain a combined wet-cake product of acceptable purity.

A still further embodiment of the process of the present invention for producing and recovering two wet-cake products comprising crystalline N-(phosphonomethyl)glycine product from an oxidation reaction solution comprising dissolved N-(phosphonomethyl)glycine product and impurities is shown in FIG. 6. In this embodiment, impurity distribution among the crystalline N-(phosphonomethyl) glycine wet-cake products is managed by net transfer of impurities contained in one of the first and second mother liquor fractions to: (i) the other of the first and second crystallization operations; (ii) the other of the first and second liquid/solids separation steps; (iii) the other of the first and second wet-cake products; or any combination of (i), (ii) and/or (iii).

Referring now to FIG. 6, an aqueous feed stream 101 comprising an N-(phosphonomethyl)iminodiacetic acid substrate is introduced along with oxygen into an oxidation reactor system 103 comprising one or more oxidation reaction zone(s), wherein the N-(phosphonomethyl)iminodiacetic acid substrate is oxidatively cleaved in the presence of a catalyst to form an oxidation reaction solution 105. The oxidation reaction solution 105 withdrawn from the reactor system 103 is then divided into plural fractions and a portion 107 (i.e., a primary fraction of the oxidation reaction solution) is introduced into an adiabatic crystallizer 111 to produce a primary product slurry 113 comprising precipitated N-(phosphonomethyl)glycine product crystals and primary mother liquor. Another portion 109 (i.e., a secondary fraction of the oxidation reaction solution) is introduced into a non-adiabatic heat-driven evaporative crystallizer 125 to produce an evaporative crystallization slurry 126 (i.e., a secondary product slurry) comprising precipitated N-(phosphonomethyl)glycine product crystals and secondary mother liquor.

Operation of the adiabatic crystallizer 111 produces vapor 115 (i.e., the adiabatic crystallizer overhead) discharged from the top of the crystallizer, a decantate (i.e., primary mother liquor) stream 112 withdrawn from the crystallizer and a primary crystallization product slurry 113 removed from the bottom of the crystallizer and comprising precipitated crystalline N-(phosphonomethyl)glycine product and primary mother liquor. Preferably, at least a portion (and more preferably all) of the adiabatic crystallizer overhead 115 and/or decantate 112 withdrawn from the adiabatic crystallizer 111 is/are recycled back to the oxidation reactor system 103.

The primary crystallization product slurry 113 comprising precipitated crystalline N-(phosphonomethyl)glycine product and primary mother liquor removed from the bottom of the adiabatic crystallizer is introduced into a liquid/solids separation device 117, preferably a basket centrifuge or bank of basket centrifuges, to produce a wet-cake product 119 and a solids-depleted stream 123 (e.g., centrate). At least a portion of the solids-depleted stream 123 may be recycled back to the adiabatic crystallizer 111 and/or optionally may be recycled back to the oxidation reactor system 103 as shown by the dashed line in FIG. 6. Preferably, the wet-cake product 119 has a solids content of from about 90% to about 99% by weight as described above.

In the operation of the non-adiabatic evaporative crystallizer 125, heat is transferred to secondary fraction 109 to vaporize water (and small molecule impurities, such as formaldehyde and formic acid) and form a non-adiabatic crystallizer overhead vapor stream 127. The N-(phosphonomethyl)glycine product precipitates to produce an evaporative crystallization slurry 126 comprising precipitated crystalline N-(phosphonomethyl)glycine product and secondary mother liquor. Slurry 126 is withdrawn from the non-adiabatic evaporative crystallizer 125, and divided into plural fractions comprising a first fraction 129 and a second fraction 131. First fraction 129 is introduced into a first liquid/solids separation device 133, preferably a solid bowl centrifuge, to produce a first fraction wet-cake product 153 having a solids content of from about 70% to about 85% by weight as described above and a solids-depleted stream 134 (e.g., centrate). The solids-depleted stream is typically recycled back to the non-adiabatic evaporative crystallizer. However, at least a portion of the solids-depleted stream 134 can optionally be mixed back with the wet-cake as shown by the dashed line in FIG. 6 to generate a first fraction wet-cake product 153A of even lower solids content. The first fraction wet-cake product 153 or 153A is then preferably blended with the wet-cake product 119 produced from the adiabatic crystallizer to produce first wet-cake product 121.

The second fraction 131 of the evaporative product slurry is optionally introduced into a hydroclone (or bank of hydroclones) 135 to form a concentrated second slurry fraction 137 enriched in precipitated N-(phosphonomethyl) glycine product and a solids-depleted stream 139. The hydroclone solids-depleted stream 139 is preferably recycled back to the heat-driven evaporative crystallizer 125 for further recovery of the N-(phosphonomethyl)glycine product. The concentrated second fraction 137 is introduced into a separator feed tank 141, which feeds a liquid/solids separation device, preferably a basket centrifuge capable of producing a wet-cake product having a relatively high solids content (typically from at least about 85% to about 99% by weight solids). In the preferred embodiment shown in FIG.

6, the concentrated second slurry fraction 137 is introduced into a bank of basket centrifuges operated in parallel. Thus, the concentrated slurry accumulated in the separator feed tank 141 is divided into concentrated slurry fractions 143A and 143B that are introduced into basket centrifuges 145A and 145B, respectively. The basket centrifuges each produce a product wet-cake 149A and 149B that are combined to form the second wet-cake product 151. The basket centrifuges further produce centrates 147A and 147B that are further depleted in precipitated product and may be recycled back to the non-adiabatic evaporative crystallizer 125. Alternatively, if necessary to obtain a wet-cake product of acceptable purity, at least a portion of centrates 147A, 147B and/or 134 may be purged from the process.

As shown in FIG. 6, at least some options for management of impurity distribution by net transfer of impurities contained in mother liquor may include, without limitation: transfer of primary mother liquor from the adiabatic crystallization (e.g., decantate 112 and/or the solids-depleted stream 123) to evaporative crystallization operation 125; transfer of centrates 147A and/or 147B to first wet-cake product 121; transfer of centrates 147A and/or 147B to adiabatic crystallizer 111; and/or transfer of centrates 147A and/or 147B to primary product slurry 113.

It is expected that the N-(phosphonomethyl)glycine product crystals generated in the adiabatic crystallizer system will be larger. This provides a material having good handling characteristics when blended with wet-cake from the non-adiabatic crystallizer system. However, the blended wet-cake might not allow for as much entrained liquid. Therefore it might be desired to grind the adiabatic crystals to make a smaller crystal size, either to give a more uniform crystal size distribution within the blended material or to ensure a suitable amount of entrained liquid with the blended wet-cake for impurity balance reasons.

EXAMPLES

The following examples are simply intended to further illustrate and explain the present invention. The invention, therefore, should not be limited to any of the details in these examples.

Example 1

A sample of N-(phosphonomethyl)glycine wet-cake was submitted for analysis and subsequent testing. The wet-cake was obtained from a non-adiabatic evaporative crystallizer stage used to dewater a product slurry obtained from catalytic oxidation of N-(phosphonomethyl)iminodiacetic acid and was subjected to a subsequent centrifuge wash cycle. The dried sample was analyzed for impurities, namely, formaldehyde, formic acid, N-methyl-N-(phosphonomethyl)glycine (NMG), aminomethylphosphonic acid (AMPA), methyl aminomethylphosphonic acid (MAMPA), iminodiacetic acid (IDA), glycine, imino-bis-(methylene)-bis-phosphonic acid (iminobis) and N-(phosphonomethyl) iminodiacetic acid (GI) and also for N-(phosphonomethyl) glycine content.

The sample was then separated into 3 separate equal weight fractions, and each of these was reslurried into room temperature water at 3 different mass ratios—3:1, 7:1, and 15.67:1 water to dry solid. These ratios are 1 to 2 order of magnitude higher than the typical water displacement ratios during a centrifuge wash step, but insufficient to fully dissolve the solids. After a length of time, the solid samples were filtered, dried, and re-submitted for analysis. The intent of the test was to find which impurities could be washed off the solids and which were "occluded" as solid phase impurities. Table 1 below shows each of the residual solid phase impurities that could not be washed away by the re-pulp water washes. The other impurities in the wet-cake were believed to be washed away during the re-pulping. The data is shown in units of residual ppm impurity per weight percent N-(phosphonomethyl)glycine (Gly) in the solid phase. Only minimal purity increases could be achieved by this method.

TABLE 1

| Water/ Solid Ratio | GI/Gly Ratio Ppm/% | Iminobis/ Gly Ratio ppm/% | MAMPA/ Gly Ratio ppm/% | AMPA/ Gly Ratio ppm/% | IDA/Gly Ratio ppm/% | Glycine/ Gly Ratio ppm/% |
|---|---|---|---|---|---|---|
| 0 | 21.4 | 110.6 | 46.9 | 87.0 | 22.5 | 13.8 |
| 3:1 | 20.6 | 98.1 | 41.7 | 76.5 | 16.5 | 9.5 |
| 7:1 | 20.7 | 97.4 | 41.3 | 75.2 | 17.6 | 9.4 |
| 15.67:1 | 20.9 | 94.9 | 41.9 | 72.7 | 16.8 | 8.9 |

The above solid phase impurities constituted between 256.1 ppm per weight percent N-(phosphonomethyl)glycine and 302.2 ppm per weight percent N-(phosphonomethyl) glycine in the solid phase. To convert these values to weight percent impurities in the dry wet-cake, the sum of the values in Table 1 for any given row is divided by 10,000 (this is defined as X), and this resultant value is divided by 1-X. Performing this arithmetic shows that an impurity level of 3.12 weight percent was contained in the dry wet-cake before water re-pulp, and 2.63 weight percent remained after much washing. It should be understood that this implies a N-(phosphonomethyl)glycine content of 96.9 to 97.4 weight percent in the wet-cake in this example.

Example 2

An experiment was conducted using a system similar to that illustrated in FIG. 3 to produce and recover N-(phosphonomethyl)glycine wet-cake products. Varying proportions 113B of the primary product slurry 113 from the adiabatic crystallizer were blended with the fraction 137 of the evaporative crystallization slurry 126 (i.e., secondary product slurry) from the evaporative crystallizer in the evaporative centrifuge feed tank 141. During this experiment, the ratio of primary fraction 107 to the oxidation reaction solution 105 averaged about 0.79, while the concentration of N-(phosphonomethyl)glycine dissolved in solution 105 averaged about 9% by weight. The solids content in primary product slurry 113 was maintained at about 25% by weight, while that in secondary product slurry 126 was maintained at about 11% by weight.

During the course of the experiment, the mass ratio of solids from the portion 113B of the primary product slurry to the combined solids in 143 was varied from 0 to about 0.40 in increments of approximately 0.10. Initially, prior to blending material from the primary product slurry 113 from the adiabatic crystallizer with the fraction 137 of the secondary product slurry from the evaporative crystallizer, the fraction 129 of the secondary product slurry fed to the solid bowl centrifuge 133 averaged about 37% by weight, but was increased to about 55% by weight by the end of the experiment, while still achieving the same wet-cake production relative to total production (i.e., from about 15% to about 16%). At each mass ratio of solids from the portion 113B of the primary product slurry to the combined solids in 143, the amount of centrifuge wash water was reduced until the N-(phosphonomethyl)glycine purity of the combined wet-cakes 149A and 149B matched that of the previous ratio. A ratio was ultimately reached where water wash was totally eliminated, yet the N-(phosphonomethyl)glycine assay of the combined wet-cakes 149A and 149B exceeded that obtained prior to blending material from the primary product slurry 113 from the adiabatic crystallizer with the fraction 137 of the secondary product slurry from the evaporative crystallizer. The N-(phosphonomethyl)glycine assay in the combined wet-cakes 149A and 149B went from 95.9 to 96.4% by weight (dry basis).

Example 3

A process material balance model was created and utilized to simulate and compare the product recovery systems as illustrated in FIGS. 2, 3 and 5. All model simulations made the following assumptions and inputs.

The system is operated at steady-state and the same base feed amount of N-(phosphonomethyl)iminodiacetic acid (GI) in aqueous feed stream 101 is fed to the oxidation reactor system 103. Feed water in aqueous feed stream 101 is adjusted to keep the N-(phosphonomethyl)glycine (Gly) concentration constant at 9.1% by weight in the reaction solution 105 exiting the reactor system 103. The concentration of unreacted N-(phosphonomethyl)iminodiacetic acid in oxidation reaction solution 105 is 900 ppm by weight. The selectivity of the oxidation reactor system 103 is assumed to be such that 0.721 pounds of N-(phosphonomethyl)glycine were formed for every pound of N-(phosphonomethyl)iminodiacetic acid reacted. Additionally, the oxidation reactor system 103 is assumed to generate 0.00325 pounds of impurities for each pound of N-(phosphonomethyl)glycine formed in the oxidation reactor system. These impurities are assumed to be non-volatile in the process and remain in liquid or are occluded in crystal solids or co-crystallized.

The concentration of N-(phosphonomethyl)glycine in adiabatic crystallizer primary mother liquor decantate 112 and centrate 123 is 3.5% by weight. Solids concentration in primary adiabatic crystallization product slurry 113 is assumed to be 25% by weight. The ratio of adiabatic crystallizer overhead 115 to primary fraction 107 of the oxidation reaction solution is assumed to be 0.07. The solids content of wet-cake product 119 is 92% by weight.

All liquid/solids separation devises employed in the process are assumed to generate solid-free liquids and the decantate from the adiabatic crystallizer 111 is likewise solid-free.

The partition coefficient for N-(phosphonomethyl)iminodiacetic acid solids in adiabatic crystallizer 111 is 0.90. The N-(phosphonomethyl)iminodiacetic acid partition coefficient in the evaporative crystallizer 125 is 0.20. These N-(phosphonomethyl)iminodiacetic acid partition coefficients are defined as the ratio of the concentration of N-(phosphonomethyl)iminodiacetic acid in the solid to N-(phosphonomethyl)iminodiacetic acid in the liquid phase where the concentration in the solid phase is on a N-(phosphonomethyl)glycine-only basis. The impurities partition coefficient in evaporative crystallizer 125 with respect to non-volatile impurities generated in the oxidation reactor system is 0.60. This partition coefficient is defined as the ratio of the concentration of impurities in the solid to impurities in the liquid phase where the impurities concentration in the solid phase is on a N-(phosphonomethyl) glycine-only basis. The non-volatile impurities partition coefficient in the adiabatic crystallizer 111 is assumed to be negligible.

The solids content of secondary evaporative crystallization slurry 126 is 15% by weight. Centrates 147A, 147B and 134 contain 7% by weight N-(phosphonomethyl)glycine.

The assumed ratio of solids concentration in concentrated slurry 137 to the solids concentration in second fraction 131 of the secondary evaporative crystallization slurry is 1.7.

The solids content of first fraction wet-cake product 153 is 70% by weight and the solids content of second weight cake product 151 is 88% by weight.

In model simulations, the calculations also assume 2500 ppm by weight of volatile reaction by-products present in oxidation reactor solution 105. These volatile components can leave in the overhead streams of the adiabatic crystallizer 111 and the evaporative crystallizer 125. The concentration of volatile impurities in the respective crystallizer overheads is assumed to be equal to the concentration of volatile impurities in all the materials fed to the adiabatic crystallizer 111 and the evaporative crystallizer 125.

Case A: This is a simulated material balance for a process configuration similar to that illustrated in FIG. 2, with the second wet-cake product 151 representing 31.11 weight percent of the total N-(phosphonomethyl)glycine production. In this example, the N-(phosphonomethyl)glycine assay of the second weight cake product 151 is 95.00% by weight (dry basis) and the required non-adiabatic evaporative crystallizer overhead 127 is 2.73 pounds per pound of N-(phosphonomethyl)iminodiacetic acid feed to the reactor system 103.

Case B: This is a variation on Case A, but with the second wet-cake 151 production increased to 35.57 weight percent of the total N-(phosphonomethyl)glycine production, while keeping the overall required non-adiabatic evaporative crystallizer overhead 127 per pound of N-(phosphonomethyl) iminodiacetic acid feed to the reactor system 103 approximately the same. In this case, the N-(phosphonomethyl) glycine assay of the second wet-cake product 151 drops to 93.91% by weight (dry basis). Case B illustrates a limit in the production rate of second wet-cake product 151 having acceptable purity.

Case C: This is a further variation on Cases A and B except that the second wet-cake 151 production is further increased to 41.90% of the total N-(phosphonomethyl)glycine production and the feed water make-up in aqueous feed stream 101 is increased as more production is shifted to the non-adiabatic crystallizer 125. In this case, the N-(phosphonomethyl)glycine assay of the second wet-cake product 151 is similar to that as in Case A, but is realized at the cost of the required non-adiabatic evaporative crystallizer overhead 127 increasing to 3.69 pounds per pound of N-(phosphonomethyl)iminodiacetic acid feed to the reactor system 103. Case C illustrates how a higher production rate of second wet-cake product 151 can be achieved by shifting more production to the non-adiabatic crystallizer, but at the expense of increased non-adiabatic evaporative crystallizer overhead 127 requirements (i.e., increased non-adiabatic evaporative crystallizer operating costs).

Cases A through C illustrate that increasing the percent of second wet-cake product 151 in FIG. 2 comes at the expense of either reduced the N-(phosphonomethyl)glycine assay of the second wet-cake product 151 (Case B) and/or at the expense of additional non-adiabatic evaporative crystallizer overhead 127 requirements (Case C).

Case D: This is a simulated material balance for a process configuration similar to that illustrated in FIG. 3 wherein a portion 113B of the primary crystallization product slurry 113 from the adiabatic crystallizer 111 is transferred and mixed with evaporative crystallization slurry 126 from the non-adiabatic evaporative crystallizer 125 in the evaporative crystallizer centrifuge feed tank 141. In this case, 42% of the production can be produced as second wet-cake product 151, while the N-(phosphonomethyl)glycine assay of the second wet-cake product 151 is higher than in Case A (which produced a lower second wet-cake percentage) and non-adiabatic evaporative crystallizer overhead 127 requirements are slightly reduced as compared to Case A. This illustrates how mixing primary crystallization product slurry 113 from the adiabatic crystallizer with evaporative crystallization slurry 126 from the non-adiabatic evaporative crystallizer can yield increased second wet-cake 151 production without increasing non-adiabatic evaporative crystallizer overhead 127 requirements and/or sacrificing wet-cake purity.

Case E: This case is similar to Case D, except that in accordance with FIG. 5, wet-cake product 119 recovered by basket centrifuge 117 instead of primary crystallization product slurry 113 from the adiabatic crystallizer is transferred and mixed with evaporative crystallization slurry 126 from the non-adiabatic evaporative crystallizer 125 in the evaporative crystallizer centrifuge feed tank 141. In this case, similar second wet-cake product 151 purity and quantity is achieved as in Case D, but at a reduced non-adiabatic evaporative crystallizer overhead 127 requirement.

Table 2 below summarizes the input and model calculated values for the simulated material balance in Cases A through E.

The present invention is not limited to the above embodiments and can be variously modified. The above description of preferred embodiments is intended only to acquaint others skilled in the art with the invention, its principles and its practical application so that others skilled in the art may adapt and apply the invention in its numerous forms, as may be best suited to the requirements of a particular use.

With reference to the use of the word(s) "comprise" or "comprises" or "comprising" in this entire specification (including the claims below), it is noted that unless the context requires otherwise, those words are used on the basis and clear understanding that they are to be interpreted inclusively, rather than exclusively, and that it is intended each of those words to be so interpreted in construing this entire specification.

What is claimed is:

1. A process for recovering an N-(phosphonomethyl)glycine product from an aqueous oxidation reaction solution comprising an N-(phosphonomethyl)glycine product, the process comprising:
    dividing the aqueous reaction solution into plural fractions comprising a primary fraction and a secondary fraction;
    precipitating N-(phosphonomethyl)glycine product crystals from the primary fraction to produce a primary product slurry comprising precipitated N-(phosphonomethyl)glycine product crystals and a primary mother liquor;
    dividing said primary product slurry into a first portion and a second portion;
    separating precipitated N-(phosphonomethyl)glycine product crystals from said first portion of said primary product slurry, thereby producing a first N-(phosphonomethyl)glycine wet-cake product;
    combining said second portion of said primary product slurry with N-(phosphonomethyl)glycine product contained in said secondary fraction of said aqueous reaction solution;
    subjecting said secondary fraction of said aqueous reaction solution to an evaporative crystallization operation to precipitate N-(phosphonomethyl)glycine product crystals from said secondary fraction, thereby producing a secondary evaporative product slurry comprising precipitated N-(phosphonomethyl)glycine product crystals and a secondary mother liquor; and
    separating precipitated N-(phosphonomethyl)glycine product crystals from said secondary evaporative prod-

TABLE 2

| Case | Water in Aqueous Feed Stream 101 to Reactor System 103 (lb/ 100 lb GI)** | wt % Gly in Oxidation Reaction Solution 105* | Ratio of Primary Fraction 107 to Reaction Solution 105* | % of Primary Product Slurry 113 Sent to Feed Tank 141* | Non-Adiabatic Crystallizer Overhead 127 (lb/ lb GI)** | % of Total Production as Wet-Cake 151** | % of Wet-Cake 151 from Adiabatic Crystallizer** | Wet-Cake 151 Gly Assay (wt % dry basis)** | Wet-Cake 121 Gly Assay (wt % dry basis)** | % of Non-Adiabatic Crystallizer Slurry 126 to Solid Bowl Centrifuge 133* | Ratio of Centrate 134 Sent to Wet-Cake 121 to 134 Recycled to Non-Adiabatic Crystallizer 125* |
|---|---|---|---|---|---|---|---|---|---|---|---|
| A | 337.00 | 9.1% | 0.69 | 0.0% | 2.73 | 31.11% | 0.00% | 95.00% | 97.30% | 20% | 0.7 |
| B | 337.00 | 9.1% | 0.69 | 0.0% | 2.79 | 35.57% | 0.00% | 93.91% | 98.04% | 10% | 0.75 |
| C | 418.00 | 9.1% | 0.57 | 0.0% | 3.69 | 41.90% | 0.00% | 94.99% | 97.90% | 20% | 0.18 |
| D | 314.42 | 9.1% | 0.76 | 25.0% | 2.48 | 42.55% | 28.22% | 95.94% | 97.17% | 20% | 0.5 |
| E | 293.55 | 9.1% | 0.75 | 25.0% | 2.28 | 42.53% | 28.25% | 95.99% | 97.15% | 20% | 0.5 |

*User Inputs
**Model Calculations uct slurry, thereby producing a second N-(phosphonomethyl)glycine wet-cake product.

2. A process as set forth in claim 1, wherein the primary fraction is cooled by evaporating water therefrom under substantially adiabatic conditions to precipitate N-(phosphonomethyl)glycine product crystals from the primary fraction and produce said primary product slurry comprising precipitated N-(phosphonomethyl)glycine product crystals and primary mother liquor.

3. A process as set forth in claim 1, wherein said second portion of said primary product slurry is combined with said secondary fraction of said aqueous reaction solution to form an evaporative crystallizer feed mixture and said evaporative crystallizer feed mixture is subjected to said evaporative crystallization operation to precipitate N-(phosphonomethyl)glycine product crystals from said evaporative crystallizer feed mixture and thereby produce said secondary evaporative product slurry.

4. A process as set forth in claim 3, wherein the process further comprises:
dividing the secondary evaporative product slurry into plural fractions comprising a first fraction and a second fraction;
separating precipitated N-(phosphonomethyl)glycine product crystals from said first fraction of said secondary evaporative product slurry, thereby producing a first fraction N-(phosphonomethyl)glycine wet-cake product; and
separating precipitated N-(phosphonomethyl)glycine product crystals from said second fraction of said secondary evaporative product slurry to produce said second N-phosphonomethyl)glycine wet-cake product, the second N-(phosphonomethyl)glycine wet-cake product having a solids content greater than the first fraction wet-cake product.

5. A process as set forth in claim 4, wherein precipitated N-(phosphonomethyl)glycine product crystals are separated from said second fraction of said secondary evaporative product slurry in a basket centrifuge and precipitated N-(phosphonomethyl)glycine product crystals are separated from said first fraction of said secondary evaporative product slurry in a solid bowl centrifuge.

6. A process as set forth in claim 4, wherein the ratio of solids content of the second N-(phosphonomethyl)glycine wet-cake product to the solids content of the first fraction N-(phosphonomethyl)glycine wet-cake product, as measured by weight percent of solids in said wet-cake products, is at least about 1.1.

7. A process as set forth in claim 6, wherein the ratio of solids content of the second N-(phosphonomethyl)glycine wet-cake product to the solids content of the first fraction N-(phosphonomethyl)glycine wet-cake product, as measured by weight percent of solids in said wet-cake products, is at least about 1.2.

8. A process as set forth in claim 7, wherein the ratio of solids content of the second N-(phosphonomethyl)glycine wet-cake product to the solids content of the first fraction N-(phosphonomethyl)glycine wet-cake product, as measured by weight percent of solids in said wet-cake products, is at least about 1.25.

9. A process as set forth in claim 4, wherein the first fraction N-(phosphonomethyl)glycine wet-cake product is combined with the first N-(phosphonomethyl)glycine wet-cake product.

10. A process as set forth in claim 4, wherein N-(phosphonomethyl)glycine in the first wet-cake product or in the first fraction wet-cake product is neutralized with a base or bases to prepare an agronomically acceptable salt of N-(phosphonomethyl)glycine.

11. A process as set forth in claim 1, wherein said second portion of said primary product slurry is combined with at least a portion of said secondary evaporative product slurry to form a secondary fraction product mixture and precipitated N-(phosphonomethyl)glycine product crystals are separated from said secondary fraction product mixture to produce said second N-(phosphonomethyl)glycine wet-cake product.

12. A process as set forth in claim 11, wherein the process further comprises:
dividing the secondary evaporative product slurry into plural fractions comprising a first fraction and a second fraction;
separating precipitated N-(phosphonomethyl)glycine product crystals from said first fraction of said secondary evaporative product slurry, thereby producing a first fraction N-(phosphonomethyl)glycine wet-cake product; and
combining said second portion of said primary product slurry with said second fraction of said secondary evaporative product slurry to form said secondary fraction product mixture, the second N-(phosphonomethyl)glycine wet-cake product having a solids content greater than the first fraction wet-cake product.

13. A process as set forth in claim 12, wherein precipitated N-(phosphonomethyl)glycine product crystals are separated from said secondary fraction product mixture in a basket centrifuge and precipitated N-(phosphonomethyl)glycine product crystals are separated from said first fraction of said secondary evaporative product slurry in a solid bowl centrifuge.

14. A process as set forth in claim 12, wherein the ratio of solids content of the second N-(phosphonomethyl)glycine wet-cake product to the solids content of the first fraction N-(phosphonomethyl)glycine wet-cake product, as measured by weight percent of solids in said wet-cake products, is at least about 1.1.

15. A process as set forth in claim 14, wherein the ratio of solids content of the second N-(phosphonomethyl)glycine wet-cake product to the solids content of the first fraction N-(phosphonomethyl)glycine wet-cake product, as measured by weight percent of solids in said wet-cake products, is at least about 1.2.

16. A process as set forth in claim 15, wherein the ratio of solids content of the second N-(phosphonomethyl)glycine wet-cake product to the solids content of the first fraction N-(phosphonomethyl)glycine wet-cake product, as measured by weight percent of solids in said wet-cake products, is at least about 1.25.

17. A process as set forth in claim 12, wherein the first fraction N-(phosphonomethyl)glycine wet-cake product is combined with the first N-(phosphonomethyl)glycine wet-cake product.

18. A process as set forth in claim 12, wherein N-(phosphonomethyl)glycine in the first wet-cake product or in the first fraction wet-cake product is neutralized with a base or bases to prepare an agronomically acceptable salt of N-(phosphonomethyl)glycine.

19. A process for recovering an N-(phosphonomethyl) glycine product from an aqueous oxidation reaction solution comprising an N-(phosphonomethyl)glycine product, the process comprising:

dividing the aqueous reaction solution into plural fractions comprising a primary fraction and a secondary fraction;

precipitating N-(phosphonomethyl)glycine product crystals from the primary fraction to produce a primary product slurry comprising precipitated N-(phosphonomethyl)glycine product crystals and a primary mother liquor;

separating precipitated N-(phosphonomethyl)glycine product crystals from said primary product slurry, thereby producing a first N-(phosphonomethyl)glycine wet-cake product;

combining at least a portion of said first N-(phosphonomethyl)glycine wet-cake product with N-(phosphonomethyl)glycine product contained in said secondary fraction of said aqueous reaction solution;

subjecting said secondary fraction of said aqueous reaction solution to an evaporative crystallization operation to precipitate N-(phosphonomethyl)glycine product crystals from said secondary fraction, thereby producing a secondary evaporative product slurry comprising precipitated N-(phosphonomethyl)glycine product crystals and a secondary mother liquor;

separating precipitated N-(phosphonomethyl)glycine product crystals from said secondary evaporative product slurry, thereby producing a second N-(phosphonomethyl)glycine wet-cake product.

20. A process as set forth in claim 19, wherein the primary fraction is cooled by evaporating water therefrom under substantially adiabatic conditions to precipitate N-(phosphonomethyl)glycine product crystals from the primary fraction and produce said primary product slurry comprising precipitated N-(phosphonomethyl)glycine product crystals and primary mother liquor.

21. A process as set forth in claim 19, wherein at least a portion of said first N-(phosphonomethyl)glycine wet-cake product is combined with at least a portion of said secondary evaporative product slurry to form a secondary fraction product mixture and precipitated N-(phosphonomethyl)glycine product crystals are separated from said secondary fraction product mixture to produce said second N-(phosphonomethyl)glycine wet-cake product.

22. A process as set forth in claim 21, wherein the process further comprises:
    dividing the secondary evaporative product slurry into plural fractions comprising a first fraction and a second fraction;
    separating precipitated N-(phosphonomethyl)glycine product crystals from said first fraction of said secondary evaporative product slurry, thereby producing a first fraction N-(phosphonomethyl)glycine wet-cake product; and
    combining at least a portion of said first N-(phosphonomethyl)glycine wet-cake product with said second fraction of said secondary evaporative product slurry to form said secondary fraction product mixture, the second N-(phosphonomethyl)glycine wet-cake product having a solids content greater than the first fraction wet-cake product.

23. A process as set forth in claim 22, wherein precipitated N-(phosphonomethyl)glycine product crystals are separated from said secondary fraction product mixture in a basket centrifuge and precipitated N-(phosphonomethyl)glycine product crystals are separated from said first fraction of said secondary evaporative product slurry in a solid bowl centrifuge.

24. A process as set forth in claim 22, wherein the ratio of solids content of the second N-(phosphonomethyl)glycine wet-cake product to the solids content of the first fraction N-(phosphonomethyl)glycine wet-cake product, as measured by weight percent of solids in said wet-cake products, is at least about 1.1.

25. A process as set forth in claim 24, wherein the ratio of solids content of the second N-(phosphonomethyl)glycine wet-cake product to the solids content of the first fraction N-(phosphonomethyl)glycine wet-cake product, as measured by weight percent of solids in said wet-cake products, is at least about 1.2.

26. A process as set forth in claim 25, wherein the ratio of solids content of the second N-(phosphonomethyl)glycine wet-cake product to the solids content of the first fraction N-(phosphonomethyl)glycine wet-cake product, as measured by weight percent of solids in said wet-cake products, is at least about 1.25.

27. A process as set forth in claim 22, wherein the first fraction N-(phosphonomethyl)glycine wet-cake product is combined with the first N-(phosphonomethyl)glycine wet-cake product.

28. A process as set forth in claim 22, wherein N-(phosphonomethyl)glycine in the first wet-cake product or in the first fraction wet-cake product is neutralized with a base or bases to prepare an agronomically acceptable salt of N-(phosphonomethyl)glycine.

29. A process as set forth in claim 19, wherein at least a portion of said first N-(phosphonomethyl)glycine wet-cake product is combined with said secondary fraction of said aqueous reaction solution to form an evaporative crystallizer feed mixture and said evaporative crystallizer feed mixture is subjected to said evaporative crystallization operation to precipitate N-(phosphonomethyl)glycine product crystals from said evaporative crystallizer feed mixture and thereby produce said secondary evaporative product slurry.

30. A process as set forth in claim 29, wherein the process further comprises:
    dividing the secondary evaporative product slurry into plural fractions comprising a first fraction and a second fraction;
    separating precipitated N-(phosphonomethyl)glycine product crystals from said first fraction of said secondary evaporative product slurry, thereby producing a first fraction N-(phosphonomethyl)glycine wet-cake product; and
    separating precipitated N-(phosphonomethyl)glycine product crystals from said second fraction of said secondary evaporative product slurry to produce said second N-phosphonomethyl)glycine wet-cake product, the second N-(phosphonomethyl)glycine wet-cake product having a solids content greater than the first fraction wet-cake product.

31. A process as set forth in claim 30, wherein precipitated N-(phosphonomethyl)glycine product crystals are separated from said second fraction of said secondary evaporative product slurry in a basket centrifuge and precipitated N-(phosphonomethyl)glycine product crystals are separated from said first fraction of said secondary evaporative product slurry in a solid bowl centrifuge.

32. A process as set forth in claim 30, wherein the ratio of solids content of the second N-(phosphonomethyl)glycine wet-cake product to the solids content of the first fraction N-(phosphonomethyl)glycine wet-cake product, as measured by weight percent of solids in said wet-cake products, is at least about 1.1.

33. A process as set forth in claim 32, wherein the ratio of solids content of the second N-(phosphonomethyl)glycine wet-cake product to the solids content of the first fraction N-(phosphonomethyl)glycine wet-cake product, as measured by weight percent of solids in said wet-cake products, is at least about 1.2.

34. A process as set forth in claim 33, wherein the ratio of solids content of the second N-(phosphonomethyl)glycine wet-cake product to the solids content of the first fraction N-(phosphonomethyl)glycine wet-cake product, as measured by weight percent of solids in said wet-cake products, is at least about 1.25.

35. A process as set forth in claim 30, wherein the first fraction N-(phosphonomethyl)glycine wet-cake product is combined with the first N-(phosphonomethyl)glycine wet-cake product.

36. A process as set forth in claim 30, wherein N-(phosphonomethyl)glycine in the first wet-cake product or in the first fraction wet-cake product is neutralized with a base or bases to prepare an agronomically acceptable salt of N-(phosphonomethyl)glycine.

37. A process for recovering an N-(phosphonomethyl) glycine product from an aqueous oxidation reaction solution comprising an N-(phosphonomethyl)glycine product, the process comprising:
dividing the aqueous reaction solution into plural fractions comprising a primary fraction and a secondary fraction;
precipitating N-(phosphonomethyl)glycine product crystals from the primary fraction to produce a primary product slurry comprising precipitated N-(phosphonomethyl)glycine product crystals and a primary mother liquor;
precipitating N-(phosphonomethyl)glycine product crystals from a secondary crystallization feed mixture comprising said secondary fraction of said aqueous reaction solution and at least a portion of said primary product slurry to produce a secondary product slurry comprising precipitated N-(phosphonomethyl)glycine product crystals and a secondary mother liquor; and
separating precipitated N-(phosphonomethyl)glycine product crystals from said secondary product slurry, thereby producing an N-(phosphonomethyl)glycine wet-cake product.

38. A process for recovering an N-(phosphonomethyl) glycine product from an aqueous oxidation reaction solution comprising an N-(phosphonomethyl)glycine product, the process comprising:
dividing the aqueous reaction solution into plural fractions comprising a primary fraction and a secondary fraction;
precipitating N-(phosphonomethyl)glycine product crystals from the primary fraction to produce a primary product slurry comprising precipitated N-(phosphonomethyl)glycine product crystals and a primary mother liquor;
precipitating N-(phosphonomethyl)glycine product crystals from an aqueous secondary crystallization feed mixture comprising said secondary fraction of said aqueous reaction solution to produce a secondary product slurry comprising precipitated N-(phosphonomethyl)glycine product crystals and a secondary mother liquor;
combining at least a portion of said primary product slurry with at least a portion of said secondary product slurry to produce a secondary fraction product mixture; and
separating precipitated N-(phosphonomethyl)glycine product crystals from said secondary fraction product mixture, thereby producing an N-(phosphonomethyl) glycine wet-cake product.

39. A process for recovering an N-(phosphonomethyl) glycine product from an aqueous oxidation reaction solution comprising an N-(phosphonomethyl)glycine product, the process comprising:
dividing the aqueous reaction solution into plural fractions comprising a primary fraction and a secondary fraction;
precipitating N-(phosphonomethyl)glycine product crystals from the primary fraction in a first crystallization operation to produce a primary product slurry comprising precipitated N-(phosphonomethyl)glycine product crystals and a primary mother liquor;
precipitating N-(phosphonomethyl)glycine product crystals from the secondary fraction in a second crystallization operation to produce a secondary product slurry comprising precipitated N-(phosphonomethyl)glycine product crystals and a secondary mother liquor;
separating precipitated N-(phosphonomethyl)glycine product crystals from said primary product slurry in a first liquid/solids separation step, thereby producing a first wet-cake product and a primary mother liquor fraction;
separating precipitated N-(phosphonomethyl)glycine product crystals from said secondary product slurry in a second liquid/solids separation step, thereby producing a second wet-cake product and a secondary mother liquor fraction;
recycling at least a part of each of said mother liquor fractions so that unrecovered N-(phosphonomethyl) glycine product and impurities contained therein are reintroduced into one or both of said crystallization operations; and
maintaining the impurity content of each of said wet-cake products below a defined value, said maintaining of said impurity content comprising net transfer of impurities contained in one of said first and second mother liquor fractions to: (i) the other of said first and second crystallization operations; (ii) the other of said first and second liquid/solids separation steps; (iii) the other of said first and second wet-cake products; or any combination of (i), (ii) and/or (iii).

40. A process for preparing separate wet-cake products from a solution comprising both a product subject to crystallization from the solution and undesired impurities, the process comprising:
dividing the solution into plural fractions comprising a primary fraction and a secondary fraction;
precipitating product crystals from the primary fraction in a first crystallization operation to produce a primary product slurry comprising precipitated product crystals and a primary mother liquor;
precipitating product crystals from the secondary fraction in a second crystallization operation to produce a secondary product slurry comprising precipitated product crystals and a secondary mother liquor;
separating precipitated product crystals from said primary product slurry in a first liquid/solids separation step, thereby producing a first wet-cake product and a primary mother liquor fraction;
separating precipitated product crystals from said secondary product slurry in a second liquid/solids separation step, thereby producing a second wet-cake product and a secondary mother liquor fraction;

recycling at least a part of each of said mother liquor fractions so that unrecovered product and impurities contained therein are reintroduced into one or both of said crystallization operations; and maintaining the impurity content of each of said wet-cake products below a defined value, said maintaining of said impurity content comprising: (i) net transfer of impurities contained in one of said first and second mother liquor fractions to the other of said first and second crystallization operations; (ii) net transfer of impurities contained in one of said first and second mother liquor fractions to the other of said first and second liquid/solids separation steps; (iii) net transfer of wet-cake product of relatively low impurities content, as obtained from one of said first and second liquid/solids separation steps, to the other of said first and second crystallization operations; (iv) net transfer of wet-cake product of relatively low impurities content, as obtained from one of said first and second liquid/solids separation steps, to the other of said first and second liquid/solids separation steps; (v) net transfer of slurry of relatively low impurities content, as obtained in one of said first and second crystallization operations, to the other of said first and second crystallization operations; (vi) net transfer of slurry of relatively low impurities content, as obtained in one of said first and second crystallization operations, to the other of said first and second liquid/solids separation steps; or a combination of (i), (ii), (iii), (iv), (v) and/or (vi).

* * * * *